(12) United States Patent
Lu et al.

(10) Patent No.: US 12,365,675 B2
(45) Date of Patent: *Jul. 22, 2025

(54) STABLE HEAVY ISOTOPES IN AMIDE FUNCTIONAL GROUPS AND USES THEREOF

(71) Applicants: RISEN (SUZHOU) PHARMA TECH CO., LTD., Jiangsu (CN); SHANGHAI JUNSHI BIOSCIENCES CO., LTD., Shanghai (CN)

(72) Inventors: Jiasheng Lu, Shanghai (CN); Jiamin Gu, Suzhou (CN); Xiang Ji, Suzhou (CN); Dongqing Zhu, Suzhou (CN); Xiaolin He, Suzhou (CN); Xianqi Kong, Dollard-des-Ormeaux (CA)

(73) Assignees: RISEN (SUZHOU) PHARMA TECH CO., LTD., Suzhou (CN); SHANGHAI JUNSHI BIOSCIENCES CO., LTD, Shanghai (CN)

( * ) Notice: Subject to any disclaimer, the term of this patent is extended or adjusted under 35 U.S.C. 154(b) by 31 days.

This patent is subject to a terminal disclaimer.

(21) Appl. No.: 17/913,883

(22) PCT Filed: Mar. 25, 2021

(86) PCT No.: PCT/CA2021/050387
§ 371 (c)(1),
(2) Date: Sep. 23, 2022

(87) PCT Pub. No.: WO2021/189143
PCT Pub. Date: Sep. 30, 2021

(65) Prior Publication Data
US 2024/0000761 A1    Jan. 4, 2024

Related U.S. Application Data

(60) Provisional application No. 62/994,378, filed on Mar. 25, 2020.

(51) Int. Cl.
C07D 417/14 (2006.01)
A61K 31/4439 (2006.01)
A61K 31/565 (2006.01)
C07B 59/00 (2006.01)

(52) U.S. Cl.
CPC ........ *C07D 417/14* (2013.01); *A61K 31/4439* (2013.01); *A61K 31/565* (2013.01); *C07B 59/002* (2013.01); *C07B 2200/05* (2013.01)

(58) Field of Classification Search
CPC .................................................. C07D 417/14
See application file for complete search history.

(56) References Cited

U.S. PATENT DOCUMENTS 11,970,490 B2 * 4/2024 Lu .......................... C07C 235/16
2024/0190859 A1 * 6/2024 Lu .......................... C07C 237/06

FOREIGN PATENT DOCUMENTS

CN     111995541 A    11/2020
WO    2010029082 A1    3/2010

OTHER PUBLICATIONS

Lampkins et al., Enhanced Small-Molecule Assembly through Directional Intramolecular Forces, Org. Lett., vol. 7, No. 20, p. 4471-4474, Sep. 3, 2005.
Nagy-Smith et al., Molecular, local, and network-level basis for the enhanced stiffness of Hydrogel networks formed from coassembled racemic peptides: Predictions from Pauling and Corey, ACS Central Science, vol. 3, p. 586-597, May 31, 2017.
Louillat et al., Ruthernium-catalyzed cross-dehydrogenative ortho-N-carbazolation of diarylamines: Versatile access to unsymmetrical diamines, Angew. Chem. Int. Ed., 2014, vol. 53, No. 13, p. 3505-3509.
Terrazas et al., A direct, efficient method for the preparation of N6-Protected 15N-Labeled Adenosines, J. Org. Chem., 2004, vol. 59, No. 16, p. 5473-5475.
Iglesias et al., Isotopic labeling of metabolites in drug discovery applications, Curr. Drug Metab., Nov. 2012, vol. 13, No. 9, p. 1213-1225.
Disclosure of 13C5, 15N-Alpelisib, https://www.clearsynth.com/en/CSEK02531.html, Publishing date is unknown.
International Search Report and Written Opinion issued in corresponding International application No. PCT/CA2021/050387 on Apr. 29, 2021.

* cited by examiner

*Primary Examiner* — John S Kenyon
(74) *Attorney, Agent, or Firm* — BCF LLP

(57) ABSTRACT

There are provided isotope-enriched compounds containing stable heavy isotope-enriched amide functional groups for modulating the pharmacokinetic profile, metabolic profile, and/or delivery efficiency of a drug or prodrug, as well as its therapeutic or prophylactic efficacy and/or adverse effects. Use of the isotope-enriched amide-containing drugs and prodrugs for the treatment or prevention of disease states and conditions is also provided.

20 Claims, 6 Drawing Sheets

STABLE HEAVY ISOTOPES IN AMIDE FUNCTIONAL GROUPS AND USES THEREOF

CROSS-REFERENCE TO RELATED APPLICATIONS

This application is a U.S. National Stage Application under 35 U.S.C. § 371 of International Application No. PCT/CA2021/050387, filed Mar. 25, 2021, which claims the benefit of priority to U.S. application No. 62/994,378, filed Mar. 25, 2020, the entire contents of which are hereby incorporated by reference.

FIELD

The present disclosure relates to isotope-enriched compounds containing a stable heavy isotope-enriched amide functional group for modulating pharmacokinetic profile, metabolic profile, and/or delivery efficiency of a compound such as a drug or prodrug, and therapeutic and prophylactic uses thereof.

BACKGROUND

An amide, also known as an acid amide, is a compound with the functional group $R_mE(O)_nNR^1R^2$, where R, $R^1$ and $R^2$ are hydrogen (H) or an organic group. The most common amides are carboxamides (organic amides) where m is 1, E is carbon (C), and n is 1. Many other important types of amides are known, including phosphoramides (for example, where m is 1, E is phosphorus (P), and n is 2, and related compounds) and sulfonamides (for example, where m is 1, E is sulfur (S), and n is 2, and related compounds) (see *IUPAC*, Compendium of Chemical Terminology, 2nd ed. (the "Gold Book"), 1997). Another class of amide is the phosphonamide.

Structurally, the amide linkage in a compound can be presented as below,

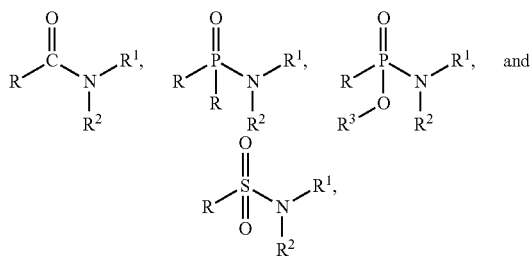

referring to carboxamide, phosphoramide, phosphonamide, and sulfonamide, respectively; where R, $R^1$, $R^2$, and $R^3$ are hydrogen or an organic group such as alkyl, cycloalkyl, heterocycloalkyl, aryl, heteroaryl, or a combination thereof, without or with a further substituent group.

In the usual nomenclature, one adds the term "amide" to the stem of the acid's name. For instance, the amide derived from acetic acid is named acetamide ($CH_3CONH_2$). IUPAC recommends naming this compound ethanamide, but this and related formal names are rarely encountered. When the amide is derived from a primary or secondary amine, the substituents on nitrogen are indicated first in the name. Thus, the amide formed from dimethylamine and acetic acid is N,N-dimethylacetamide ($CH_3CONMe_2$). Cyclic amides are called lactams; they are necessarily secondary or tertiary amides. Functional groups consisting of $-P(O)_2NR^1R^2$ and $-SO_2NR^1R^2$ are phosphonamides and sulfonamides, respectively (see *IUPAC*, Nomenclature of Organic Chemistry, Sections A, B, C, D, E, F, and H, Pergamon Press, Oxford, 1979. Rules C-821: Amides and Imides).

The amide is an important functional group present in many types of medicaments, such as local anesthetics, antiarrhythmics, and others. It is also the key linking moiety in protein and peptidic drug products (DeRuiter, J., Principles of Drug Action I, Spring 2005, Amides. Further, many of the medicaments developed in the last century are prodrugs of amines, underscoring their importance in the medical field. It is now widely accepted that amine prodrugs can have important role(s) in drug targeting, and that they are often the initial compounds that deliver a drug to its target site in stable form. Amine prodrugs are generally classified by the molecular linkage of the nitrogen atom to the nearby atoms. Amine-containing prodrugs display a variety of basic functional groups and linkages such as amide prodrugs, azo linkage prodrugs, lipid peptide prodrugs, and the like (Chandy, A., et al., Med. Chem. Drug Discov., 2013, 4 (2), 108-126; Simplicio, A. L., et al., Molecules, 2008, 13, 519-547).

For example, a large number of anti-cancer agents have amide-linkages (for example, see, Mohammed, Y. H. E. and Khanum, S. A., *Int. J. of Pharma and Bio Sci*. (2018), 9 (2), 94-124; Wang, B, et al., Drug Delivery, 2nd Ed., 2016, 475-502.). As a specific example, Alpelisib (previously BYL719, or N-(4-methyl-5-(2-(2,2,2-trifluoro-1,1-dimethylethyl)-4-pyridinyl)-2-thiazolyl)aminocarbonyl-L-prolinamide) is an alpha-specific PI3K (phosphoinositide-3-kinase) inhibitor investigated clinically for the treatment of some cancers described in U.S. Pat. Nos. 8,476,268 and 8,227,462). Efficacy of alpelisib (PIQRAY™) for treatment of breast cancer was demonstrated recently in the SOLAR-1 trial for PI3KCA-altered metastatic breast cancer. The compound is also being studied clinically in patients with advanced solid tumors (Ando, Y., et al., *Cancer Science*, 2019, 110:1021-1031).

Another type of medicament containing amide functional groups is RNA interference (RNAi) therapeutics. More than 20 RNAi-based therapeutics are currently in clinical trials, and positive results from these trials have helped to bolster further attempts to develop clinically relevant RNAi therapies (Bobbin & Rossi, *Annu. Rev. Pharmacol. Toxicol.*, 2016, 56:103-22). Such new therapeutics in development include siRNA conjugates for the treatment of diseases (Weingaertner & Bethge, (2019), WO2019193144; Bethge, et al., (2019), WO2019193189; Zhang, et al., (2019), WO2019105437; Zhang, et al., (2019), WO2019105414; Nair, et al., (2019), WO2019217459; Nair, et al., (2015) US2015/0196655; Muthiah, et al., (2015) WO2015006740). Synthetic small interfering RNAs (siRNAs) can inhibit expression of disease-causing genes through post-transcriptional gene silencing mediated by the endogenous RNA interference (RNAi) pathway. siRNAs have great therapeutic potential, although efficient delivery to target cells or organs remains a challenge. Covalent conjugation of small molecule compounds to siRNAs has been used to avoid side effects resulting from the use of nonviral vectors, particles, or excipient-based delivery systems. For example, conjugation of cholesterol and other lipophilic moieties to siRNAs can result in broad biodistribution and gene silencing in multiple tissues, including liver (Nair, J. K.; et al., *J. Am. Chem. Soc.* 2014, 136, 16958-16961; Wolfrum, C.; et al., *Nat. Biotechnol.* 2007, 25, 1149). In addition, well-characterized bi- and tri-antennary GalNAc ligands can be reengineered to facilitate covalent conjugation to siRNAs (Khorev, O.; et al., *Bioorg. Med. Chem.* 2008, 16, 5216; Rensen, P. C. N.; et al., *J. Med. Chem.* 2004, 47, 5798; Valentijn, A. R. P. M.; et al., *Tetrahedron*, 1997, 53, 759; Manoharan, M.; et al., WO 2009073809, 2009).

One of the key reactions for carboxylic acid amides (also referred to as carboxylic amides and carboxamides) and peptides is hydrolysis. Hydrolysis can be acid-catalyzed, base-catalyzed, or enzyme-catalyzed, and generally yields the corresponding carboxylic acid and amine. Hydrolysis involves a tetrahedral intermediate at the carbon center after the C=O double bond becomes a C—O single bond (see, East, A. L. L., *Int. J. Chem. Kinet.*, 2018, 50 (10): 705-709), as illustrated below for acid-catalyzed hydrolysis:

directly proportional to the absolute value of the ground-state vibrational energy of the bond. This vibrational energy depends on the mass of the atoms that form the bond and increases as the mass of one or both of the atoms making the bond increases. Deuterium is a stable and non-radioactive isotope of hydrogen which has approximately twice the mass of protium, which is the most common isotope of hydrogen. Since deuterium (D) has twice the mass of protium ($^1$H), a carbon-deuterium (C-D) bond is stronger than the corresponding carbon-protium (C-$^1$H) bond. If a C-$^1$H bond is broken during a rate-determining step of a metabolic reaction, then substituting a deuterium for that protium may cause a decrease in the reaction rate. In this way, D can have a significant isotopic effect.

1.

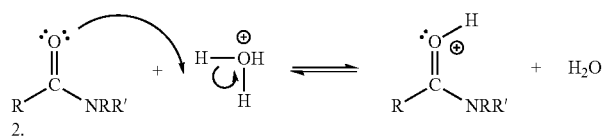

2.

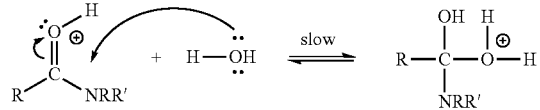

3.

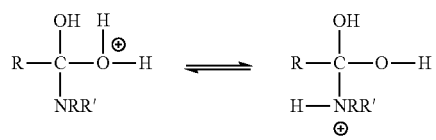

4.

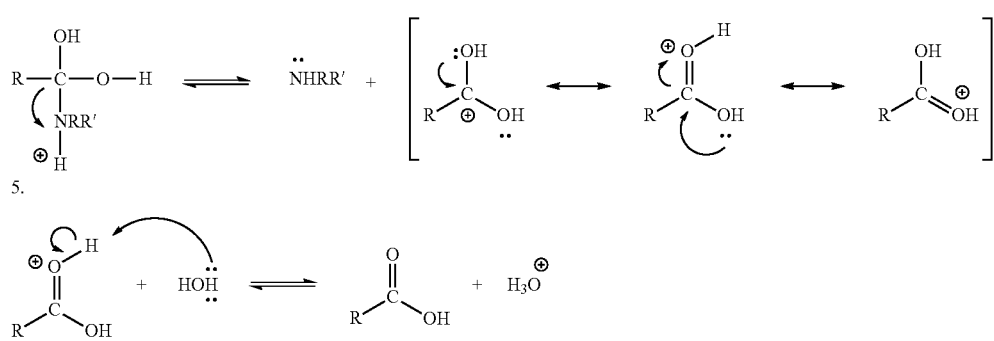

5.

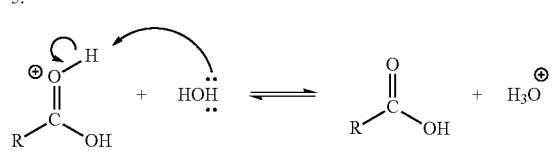

The rate-determining step is step 2, where the C=O double bond becomes a C—O single bond by cleavage of the π-bond, which has a direct effect on the rate of amide-bond cleavage.

Foreign substances including compounds and other therapeutic agents are often metabolized, to facilitate their elimination from the body. For example, various enzymes such as cytochrome P450 enzymes, esterases, proteases, reductases, dehydrogenases, transaminases, and monoamine oxidases, can react with compounds and therapeutic agents and catalyze their conversion to more polar metabolites for renal excretion. The resultant metabolites can have substantially different pharmacokinetic, pharmacodynamic, and acute and long-term toxicity profiles relative to the parent compounds.

In some cases, such metabolic reactions may involve the oxidation of a carbon-hydrogen bond to a carbon-oxygen or a carbon-carbon π-bond. Carbon-hydrogen bond strength is Deuteration of pharmaceuticals to improve pharmacokinetics and pharmacodynamics has been demonstrated. For example, SD-809, a deuterated drug (tetrabenazine-d6 or deutetrabenazine), has been used for the treatment of Huntington's disease and tardive dyskinesia. Donafenib, a deuterated version of Sorafenib, has been tested clinically for treatment of colorectal cancer and thyroid cancer. Isotope-enrichment can potentially affect a therapeutic agent's metabolism, release from prodrugs and derivatives, absorption, and/or clearance, significantly altering the agent's pharmacokinetic profile.

Isotopes are atoms that have the same atomic number but a different mass number. Many elements have more than one stable isotope. Common elements having more than one stable isotope include hydrogen, boron, carbon, nitrogen, oxygen, chlorine, magnesium, silicon, sulfur, potassium, calcium, titanium, chromium, iron, nickel, zinc, selenium, and bromine. Some elements have two or more isotopes with similar natural abundance. For example, bromine has two stable isotopes as 79Br and $^{81}$Br with natural abundance of the two isotopes being 50.69% and 49.31, respectively. Similarly, the natural abundances of stable chlorine isotopes are 76% for $^{35}$Cl and 24% for $^{37}$Cl.

Other elements of more than one stable isotope have one major isotopic form and one or more minor isotopic forms. For such elements, isotopes differ by both (1) their atomic weight, due to the number of neutrons in the nucleus and (2) their abundance in nature. For hydrogen, the common stable isotopes are proton (H or $^1$H) and deuterium (D or $^2$H), with H the predominant isotope in nature, only 0.0115% of hydrogen being D ($^2$H). For oxygen, there are three stable isotopes: $^{16}$O, $^{17}$O and $^{18}$O. The natural occurrence of the three stable oxygen isotopes is generally 99.756%, 0.039%, and 0.205% for 160, 170, and $^{18}$O, respectively. From $^{16}$O to $^{18}$O, the number of neutrons increases by 2 (from 8 to 10), causing atomic weight to increase by 12.5%. Because the difference in atomic weight between $^{16}$O and $^{18}$O is smaller than that between D and H, replacement of $^{16}$O by $^{18}$O may have smaller isotopic effect on e.g. the metabolism of a compound than replacement of H by D in some cases.

As one of the stable isotopes, $^{18}$O has been widely used in various fields of medical sciences and general health, including as an $^{18}$O-tracer in human physiology. In studies of drug metabolism and pharmacokinetics (DMPK), $^{18}$O has been used to replace $^{16}$O for tracing drug compounds and metabolites thereof after administration, in order to achieve sensitive, accurate, and fast results. $^{18}$O is also used in studies of energy metabolism and expenditure. For example, water comprising hydrogen and $^{18}$O ("H$_2$$^{18}$O" or "oxygen-18 water") can be used. If the hydrogen atoms in H$_2$$^{18}$O are replaced by the deuterium isotope, this provides D$_2$$^{18}$O (often referred to as "doubly-labeled water" or "DLW"). Use of DLW can provide a fast and accurate method for determining energy expenditure in animals and humans; this method is based on the premise that after a dose of DLW, the two isotopes equilibrate with total body water (TBW) and then are eliminated differentially from the body. Deuterium leaves the body as water, while $^{18}$O leaves as water and carbon dioxide, thus allowing energy metabolism to be determined by measuring the rate of isotope excretion. The effect of $^{18}$O on the growth and reproduction of C-57 mice has also been studied (Wolf, D.; Cohen, H.; Meshorer, A.; Wasserman, I.; Samuel D., *Stable Isot., Proc. Int. Conf.,* 3rd (1979), 353-60). In these studies, pairs of C-57 mice breathed a highly enriched $^{18}$O-atmosphere for 112 days for 3 successive generations. No significant changes in organs were detected, and mice survived and reproduced normally, even when 60% of the oxygen in their body was replaced with $^{18}$O. The study concluded that the $^{18}$O was not harmful to mice. Indeed, $^{18}$O is safe and tolerated in the human body; it can be estimated that for an average human of 60 kg body weight, the body contains approximately 40 kg of oxygen composed of all three stable isotopes ($^{16}$O, $^{17}$O and $^{18}$O), of which approximately 80 g is $^{18}$O. Similarly, for other elements of more than one stable isotope that have one major isotopic form and one or more minor isotopic forms (such as C and N), the less abundant stable isotope(s) can be found naturally present at their level of natural abundance and are generally safe and well-tolerated.

SUMMARY

It is an object of the present invention to provide amide moieties with a modified rate of amide-bond cleavage, in order to modify the pharmacokinetic profile of amide-bond containing drugs and prodrugs, thereby modulating their therapeutic and prophylactic effects and/or adverse effects.

The present invention is based, at least in part, on the inventors' appreciation that stable heavy isotopes ($^{17}$O and/or $^{18}$O; $^{13}$C; and/or $^{15}$N), in comparison with isotopes of natural abundance ($^{16}$O, $^{12}$C, and $^{14}$N), can change the rate of amide-bond cleavage, thereby modifying the pharmacokinetic profile of amide-bond containing drugs and prodrugs, so as to modulate the therapeutic, prophylactic and/or adverse effects of amide-bond containing drugs and prodrugs.

Thus, replacement of a naturally-abundant oxygen, carbon or nitrogen isotope ($^{16}$O, $^{12}$C, or $^{14}$N) with stable heavy isotopes ($^{17}$O and/or $^{18}$O; $^{13}$C; and/or $^{15}$N) could have an isotopic effect on the rate of amide-bond cleavage. Without wishing to be limited by theory, it is believed that replacement of $^{16}$O, $^{12}$C, and/or $^{14}$N with a stable heavy isotope ("*O" or "O", representing $^{17}$O and/or $^{18}$O; "*C" or "C*", representing $^{13}$C; and/or "*N" or "N*", representing $^{15}$N) can change the rate of amide-bond cleavage. This change can modify the pharmacokinetic profile of amide-bond containing drugs and prodrugs, and thus modulate the therapeutic, prophylactic, and/or adverse effect of the drugs and prodrugs. It is noted that the carboxylic amide center involves three atoms, oxygen, carbon, and nitrogen, directly, and therefore isotopes of oxygen and/or carbon and/or nitrogen can have a direct impact on the rate of amide-bond cleavage and therefore on the therapeutic, prophylactic, and/or adverse effect of amide-bond containing drugs and prodrugs.

Accordingly, there are provided amide-bond containing drug and/or prodrug compounds with one or more heavy stable isotope(s) in the place of naturally-occurring isotope(s) in one or more carboxylic amide functional group

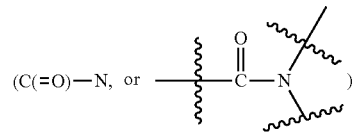

of the drug and/or prodrug compounds.

In a first broad aspect, there are provided compounds of Formula I, or pharmaceutically acceptable salts, esters, hydrates, chelates, or solvates thereof:

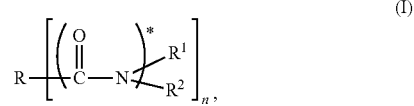

where n is an integer selected from 1 to 5;

refers to an isotope-enriched amide functional group (also referred to herein as an "isotope-enriched amide" and an "isotope-enriched amide group"); R is an organic moiety; R$^1$ and R$^2$ are independently a hydrogen or an organic moiety;

and the structure of Formula I comprises or is contained in a drug or prodrug compound containing at least one carboxamide-linkage; provided that the —NR$^1$R$^2$ moiety is not a 3-sulfo-1-propylamino moiety.

As used herein, the terms "isotope-enriched" and "heavy isotope-enriched" are used interchangeably to refer to enrichment with one or more stable heavy isotope ($^{18}$O, $^{17}$O, $^{13}$C, and/or $^{15}$N). It should be understood that where two or more atoms are enriched in a compound, the atoms may be enriched with the same or different isotopes; and in Formula I, when n>1, the multiple amide groups can be at various positions of the R group. For example, amide groups may be enriched with two different isotopes of the same element, or alternatively with isotopes of two different elements. Many such combinations and permutations are possible. When n is greater than 1, each amide group may be connected to the R group at the same or at a different position of R; or any of two amide groups can be linked via a peptide linkage (i.e., in the way that amino acids are linked in a peptide).

In one embodiment, there are provided compounds of Formula I, or pharmaceutically acceptable salts, esters, hydrates, chelates and/or solvates thereof, where the isotope-enriched amide functional group is enriched with one or more stable heavy oxygen isotope ($^{18}$O, $^{17}$O, or a mixture of $^{18}$O and $^{17}$O); and R, R$^1$ and R$^2$ are defined the same as above.

In another embodiment, there are provided compounds of Formula I, or pharmaceutically acceptable salts, esters, hydrates, chelates and/or solvates thereof, where the isotope-enriched amide functional group is enriched with one or more stable heavy carbon isotope ($^{13}$C); and R, R$^1$ and R$^2$ are defined the same as above.

In a further embodiment, there are provided compounds of Formula I, or pharmaceutically acceptable salts, esters, hydrates, chelates and/or solvates thereof, where the isotope-enriched amide functional group is enriched with one or more stable heavy nitrogen isotope ($^{15}$N); and R, R$^1$ and R$^2$ are defined the same as above.

In one embodiment, the isotope-enriched amide is enriched with a single isotope of one element, e.g., is $^{18}$O-enriched, or $^{17}$O-enriched, or $^{13}$C-enriched, or $^{15}$N-enriched.

In another embodiment, the isotope-enriched amide is enriched with two or more isotopes of one or more elements, e.g., $^{17}$O- and $^{18}$O-enriched, or $^{18}$O- and $^{13}$C-enriched, or $^{18}$O- and $^{15}$N-enriched, or $^{13}$C- and $^{15}$N-enriched.

In some embodiments of Formula I, n is an integer selected from 1 to 3.

In one embodiment of Formula I, n is 1.

In some embodiments of Formula I, the R group is alkyl, cycloalkyl, heterocycloalkyl, aryl, heteroaryl, or heterocycle.

In an embodiment, of Formula 1, the R group is an organic moiety selected from alkyl, cycloalkyl, heterocycloalkyl, aryl, heteroaryl, and heterocycle, wherein R is substituted or unsubstituted. In an embodiment of Formula I, the R group is alkyl, cycloalkyl, heterocycle, or heterocycloalkyl. In another embodiment of Formula I, the R group is alkyl, cycloalkyl or heterocycloalkyl. In another embodiment of Formula I, the R group is cycloalkyl or heterocycloalkyl. In another embodiment of Formula I, the R group is heterocycloalkyl. It should be understood that in all such embodiments of Formula I, the R group can be substituted or unsubstituted without limitation.

In an embodiment of Formula I, the R group is not fused-aromatic, e.g., not fused-aryl or fused-heteroaryl. In another embodiment of Formula I, the R group is not a 2-substituted 1H-indazol-7-yl group.

In some embodiments of Formula I, R$^1$ and R$^2$ are independently a hydrogen and a moiety selected from alkyl, cycloalkyl, heterocycloalkyl, aryl, heteroaryl, heterocycle, alkoxy, acyl and alkylthio. In an embodiment of Formula I, R$^1$ is hydrogen and R$^2$ is alkyl, alkylthio, or aryl. In an embodiment of Formula I, R$^1$ is hydrogen and R$^2$ is alkyl. In one embodiment of Formula I, R$^1$ is hydrogen and R$^2$ is C$_{1-6}$ alkyl. In another embodiment, R$^1$ and/or R$^2$ is a protecting group selected from acyl, carbonyl, thiocarbonyl, and carbamoyl. In another embodiment, R$^1$ is hydrogen and R$^2$ is a protecting group selected from acyl, carbonyl, thiocarbonyl, and carbamoyl. It should be understood that in all such embodiments of Formula I, R$^1$ and R$^2$ can be substituted or unsubstituted without limitation.

In one embodiment of Formula I, R$^1$ and R$^2$ are both hydrogen.

In a particular embodiment of Formula I, R is substituted or unsubstituted alkyl, cycloalkyl or heterocycloalkyl; R$^1$ and R$^2$ are both hydrogen; and n is 1.

In some embodiments, there is provided an isotope-enriched amide, as described herein, wherein the amide is part of a drug or prodrug. Amides are important functional groups present in numerous types of drug compounds (e.g., local anesthetics, antiarrhythmics, etc.) and can also be the key linking moiety in protein and peptidic drug products (DeRuiter, J., *Principles of Drug Action* 1, Spring 2005, Amides). A large number of drug compounds include at least one amide-linkage or amine moiety and many of the drugs developed in the last century are prodrugs of amines.

In some embodiments, the compound of the invention is isotope-enriched alpelisib, e.g., $^{18}$O-alpelisib. Alpelisib is an amide-containing drug with the following structure:

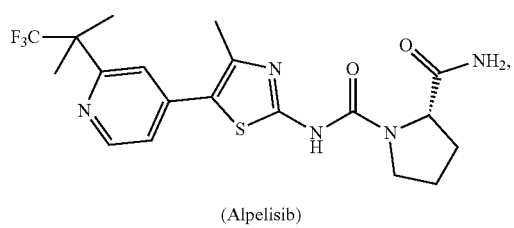 [SMILES: Cc1nc(NC(=O)N2CCC[C@H]2C(N)=O)sc1-c1ccnc(C(C)(C)C(F)(F)F)c1]

(Alpelisib)

which has an amide functional group, a prolinamide group, derived from a proline moiety as illustrated on the right end of the compound. The compound has two oxygen atoms, with one (O$_1$) in a simple amide group and the other (O$_2$) in a urea fragment.

It has been demonstrated that Alpelisib is metabolized heavily on the prolinamide group to form the corresponding proline derivative, namely the carboxylic acid (shown below; James, A. et al., *Cancer Chemother. Pharmacol.*, (2015), 76(4), 751-760)). Unfortunately, this acid metabolite ("M4") is biologically inactive.

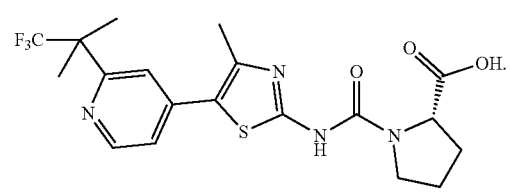

(M4, the main metabolite of Alpelisib)

In an embodiment, there is provided an isotope-enriched amide as described herein, wherein the isotope-enriched amide is contained in Alpelisib. In one embodiment, there are provided compounds of Formula I, or pharmaceutically acceptable salts, esters, hydrates, chelates, and/or solvates thereof, where R is N-((4-methyl-5-(2-(2,2,2-trifluoro-1,1-dimethylethyl)-4-pyridinyl)-2-thiazolyl)aminocarbonyl)-pyrrolidin-2-yl group, or the following moiety:

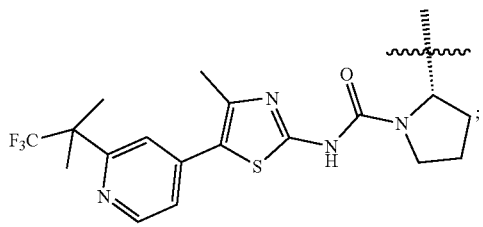 [SMILES: Cc1nc(NC(=O)N2CCC[C@H]2C)sc1-c1ccnc(C(C)(C)C(F)(F)F)c1]

and $R^1$ and $R^2$ are hydrogen or a protecting group, thus providing an Alpelisib derivative with an isotope-enriched amide functional group. Since the amide carbonyl group in Alpelisib is a C=O bond, isotope-enriched alpelisib may be isotope-enriched at the $C_1$ carbon (e.g., by replacing the $C_1$-carbon with $^{13}C$, i.e., $^{13}C_1$-alpelisib), at the $O_1$ oxygen (e.g., by replacing the $O_1$ oxygen with $^{18}O$ or $^{17}O$, i.e., $^{18}O_1$-alpelisib, $^{17}O_1$-alpelisib), or at both $C_1$ and $O_1$ (e.g., $^{13}C_1{}^{18}O_1$-alpelisib, $^{13}C_1{}^{17}O_1$-alpelisib). In an embodiment, therefore, the compound of the invention is selected from $^{13}C_1$-alpelisib, $^{18}O_1$-alpelisib, $^{17}O_1$-alpelisib, $^{13}C_1{}^{18}O_1$-alpelisib and $^{13}C_1{}^{17}O_1$-alpelisib.

In one embodiment, the compound of Formula I is $^{18}O_1$-alpelisib (also referred to herein as Alpelisib-$^{18}O_1$).

In another embodiment, there is provided a compound of Formula I which is a compound of Formula IL, or a pharmaceutically acceptable salt, ester, hydrate, chelate, or solvate thereof:

(II)

where

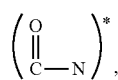

$R^1$, and $R^2$ are as defined above.

In some embodiments, the isotope-enriched amide functional group or

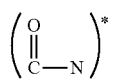

in the compound of Formula II is single isotope enriched, e.g., $^{18}O$-enriched, or $^{17}O$-enriched, or $^{13}C$-enriched, or $^{15}N$-enriched; and $R^1$ and $R^2$ are defined the same as above.

In another embodiment, the isotope-enriched amide functional group or

in the compound of Formula II is an amide functional group enriched with two or more heavy isotopes of one or more elements, e.g., $^{17}O$- and $^{18}O$-enriched, or $^{18}O$- and $^{13}C$-enriched, or $^{18}O$- and $^{15}N$-enriched, or $^{13}C$- and $^{15}N$-enriched, or $^{17}O$- and $^{13}C$-enriched, or $^{17}O$- and $^{15}N$-enriched.

In one embodiment, the compounds having an isotope-enriched amide functional group include Niraparib and Mefuparib, both being PARP inhibitors for the treatment of cancers, and the organic moiety, R in Formula I, is

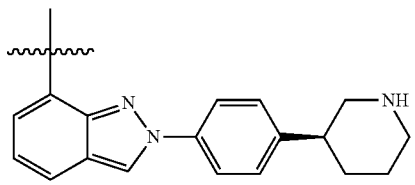 [SMILES: *c1cccc2cn(-c3ccc([C@@H]4CCCNC4)cc3)nc12]

for Niraparib and

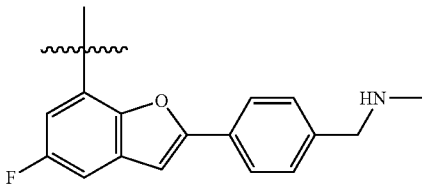 [SMILES: *c1cc(F)cc2cc(-c3ccc(CNC)cc3)oc12]

for Mefuparib, respectively. And accordingly, the corresponding isotope-enriched drugs have the following structures: (Niraparib),

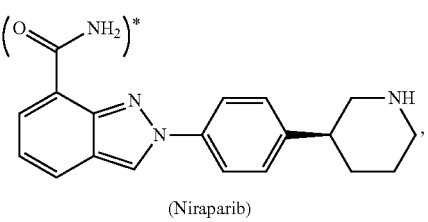

(Niraparib)

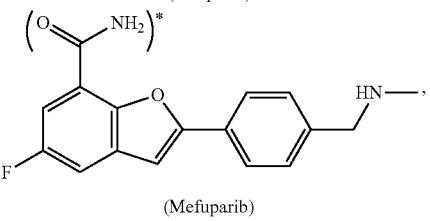

(Mefuparib)

where

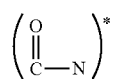

in the compounds is an amide functional group enriched with two or more heavy isotopes of one or more elements, e.g., $^{17}$O- and $^{18}$O-enriched, or $^{18}$O- and $^{13}$C-enriched, or $^{18}$O- and $^{15}$N-enriched, or $^{13}$C- and $^{15}$N-enriched, or $^{17}$O- and $^{13}$C-enriched, or $^{17}$O- and $^{15}$N-enriched.

In an alternate embodiment, the compound having an isotope-enriched amide functional group is not Niraparib, i.e., R in Formula I is not

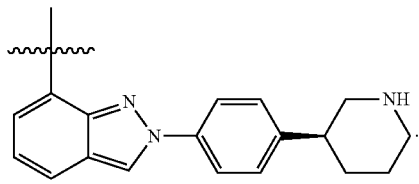 [SMILES: *c1cccc2cn(-c3ccc([C@@H]4CCCNC4)cc3)nc12]

In one particular embodiment, the compound having an isotope-enriched amide functional group is not $^{14}$C-Niraparib. In one particular embodiment, the compound having an isotope-enriched amide functional group is not $^{18}$O-Niraparib. In one particular embodiment, the compound having an isotope-enriched amide functional group is not $^{13}$C-Niraparib. In one particular embodiment, the compound having an isotope-enriched amide functional group is not $^{17}$O-Niraparib.

Another example of an amide-containing drug which may comprise an isotope-enriched amide functional group as described herein is Selexipag or Uptravi®, a drug developed by Actelion for the treatment of pulmonary arterial hypertension (PAH). Selexipag and its active metabolite, ACT-333679 (or MRE-269, the free carboxylic acid), are agonists of the prostacyclin receptor, which leads to vasodilation in the pulmonary circulation (Sitbon, O.; Morrell, N., *Eur. Respir. Rev.*, 2012, 21(126): 321-327). Selexipag is a prodrug, which is hydrolyzed to release its active species as shown below:

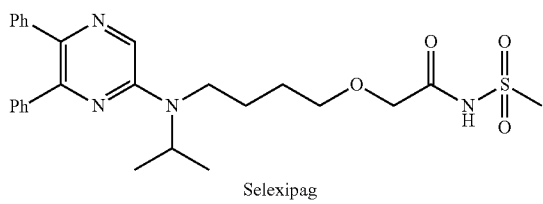

Selexipag

Hydrolysis ↓

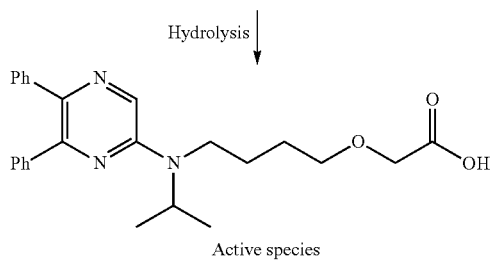

Active species

A further example of an amide-containing drug which may comprise an isotope-enriched amide functional group as described herein is Midodrine, which is an N-glycyl derivative of Desglymidodrine. The former is deprotected by peptidases to give the latter, as shown below:

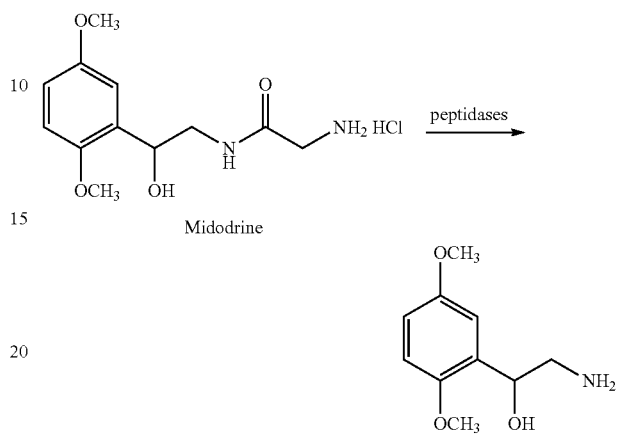

Another example of amide-containing drugs or prodrugs is NSAID prodrugs (for example, see Husain A., et al., *Sch. Acad. J. Pharm.*, 2015; 4(3): 145-152), illustrated with the following general structure:

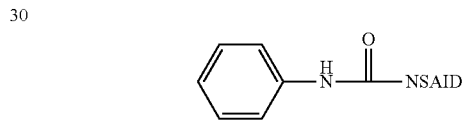

where NSAID includes without limitation Aceclofenac, Diclofenac, Fenbufen, Indomethacin, Mefenamic acid, and 4-Biphenyl acetic acid.

In another embodiment, there are provided compounds of Formula III, or pharmaceutically acceptable salts, esters, hydrates, chelates, and/or solvates thereof:

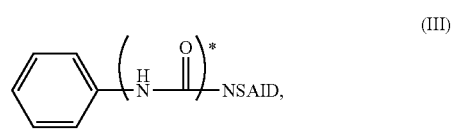

where

is as defined above; and NSAID is a residual moiety, which, together with the carboxyl group to which it is attached, forms a nonsteroidal anti-inflammatory drug (NSAID) compound.

In one embodiment, isotope-enriched amide containing compounds are Rapastinel (GLYX-13, a NMDA receptor modulator), Safinamide (a monoamine oxidase inhibitor), and/or BPN14770 (2-(4-((2-(3-chlorophenyl)-6-(trifluoromethyl)pyrimidin-4-yl)amino)phenyl)acetamide, a PDE4 allosteric modulator). The corresponding non-isotope-enriched drug structures are given below:

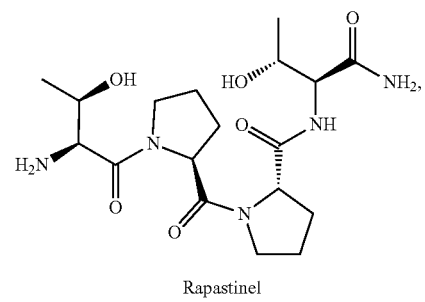
Rapastinel

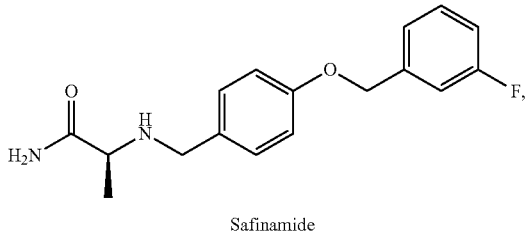
Safinamide

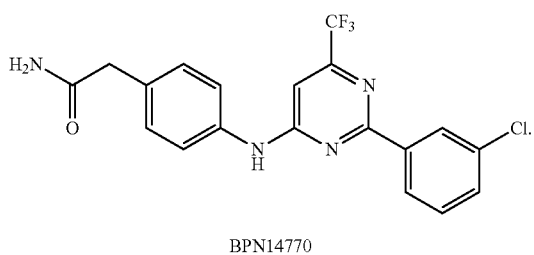
BPN14770

In another embodiment, an amide-containing drug comprises an isotope-enriched amide functional group wherein one or more of the O—, N—, and C-atoms in the amide functional group is enriched or labelled isotopically, the amide-containing drug being one of the following:

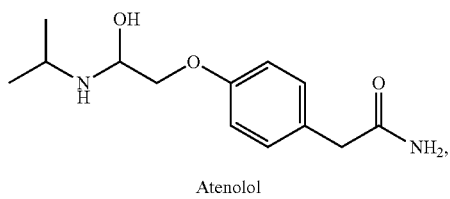
Atenolol

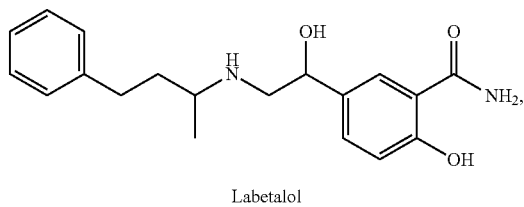
Labetalol

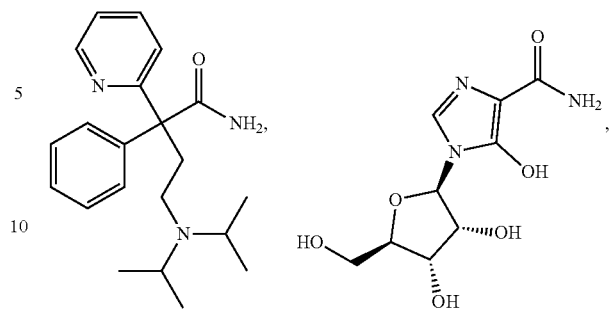
Disopyramide          Mizoribine

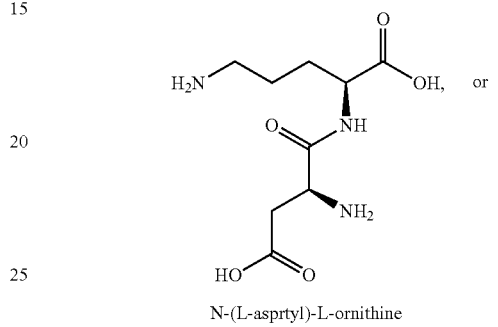
N-(L-asprtyl)-L-ornithine

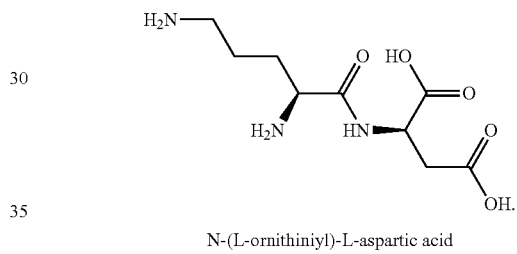
N-(L-ornithiniyl)-L-aspartic acid

It should be understood that the heavy stable isotopic effect can also be applied to esters, such as when an ester functional group becomes critical during the generation of a new chemical entity through ester hydrolysis, such as in the case of carboxylic ester (RCOOR') or phosphoric ester (ROP(O)(OR')OR"). Accordingly, there are provided ester-containing drug and/or prodrug compounds with one or more heavy stable isotope(s) in the place of naturally-occurring isotope(s) in one or more carboxylic ester or phosphoric ester functional group of the drug and/or prodrug compounds. In some embodiments, there is provided an isotope-enriched ester, wherein the ester is part of a drug or prodrug.

In further embodiments, the present technology can be applied to RNA interference (RNAi) therapeutics, such as, without limitation, synthetic small interfering RNAs (siRNAs), including siRNA-drug and/or -prodrug conjugates and GalNAc-siRNA conjugates.

Bi-and tri-antennary GalNAc ligands can be covalently conjugated to siRNAs (see, for example, Khorev, O.; et al., Bioorg. Med. Chem. 2008, 16, 5216; Rensen, P. C. N.; et al., J. Med. Chem. 2004, 47, 5798; Valentijn, A. R. P. M.; et al., Tetrahedron, 1997, 53, 759; Manoharan, M.; et al., WO 2009073809, 2009). Examples of synthesis of such siRNA-GalNAc conjugates can be found in, for example, Nair, J. K. et al., J. Am. Chem. Soc. 2014, 136, 16958-16961), as follows:

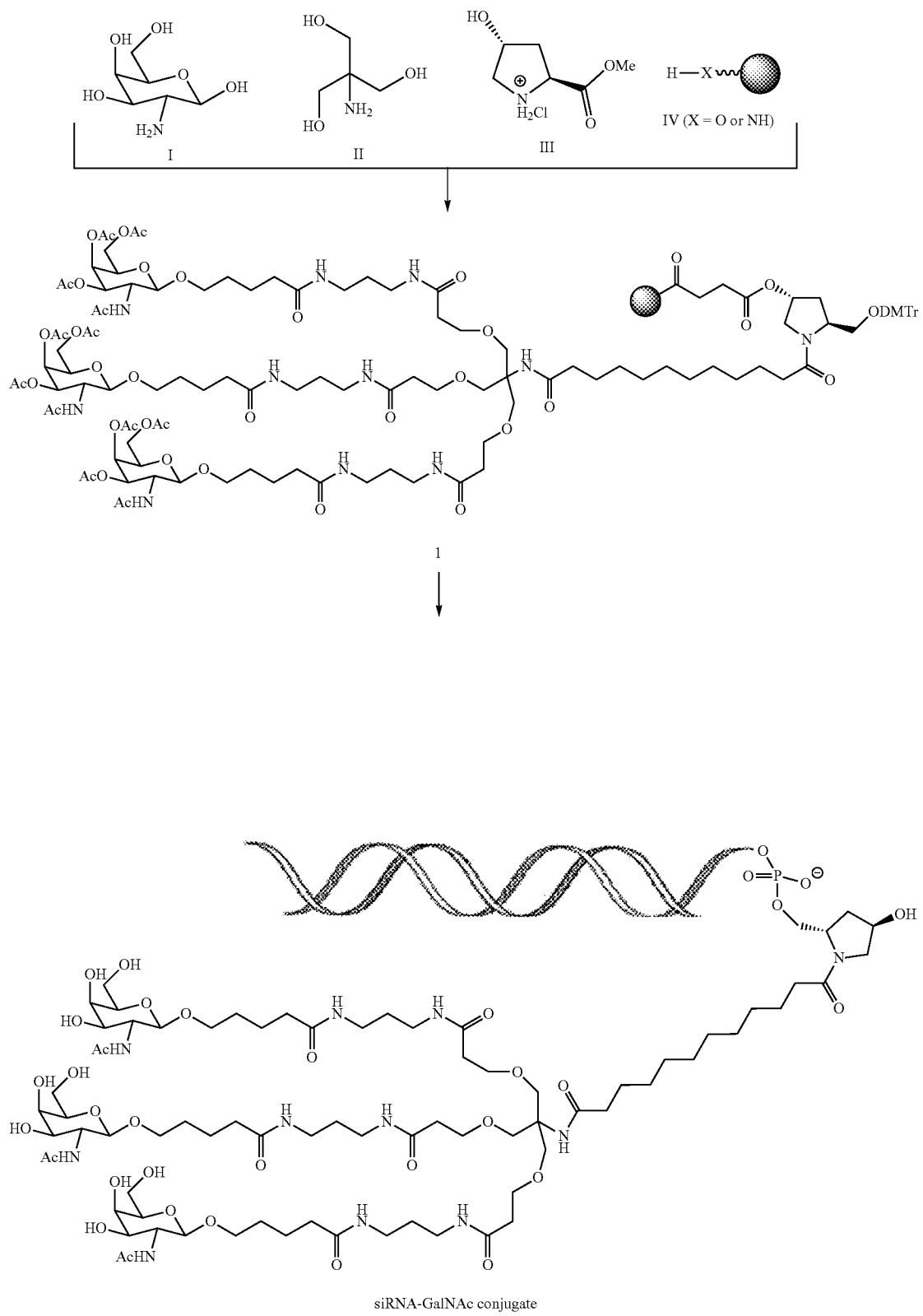
siRNA-GalNAc conjugate
J. Am. Chem. Soc. 2014, 136, 16958-16961

Nair, J. K. et al. designed various GalNAc-siRNA conjugates (*Nucleic Acids Research,* 2017, 45(19), 10969-10977), which are shown in the table below:

| Compound | Strand | Sequence (5' to 3') | L |
|---|---|---|---|
| siTTR-1 | S | AaCaGuGuUcUuGc UcUaUaAL | |
| | AS | uUaUa-GaGcAaGa AcAcUgUu*U*u | |
| siTTR-2 | S | A*a*CaGuGuUCUu GcUcUaUaAL | |
| | AS | u*U*aUaGaGcAaga AcAcUgUu*u*u | |
| siAT-1 | S | GgUuAaCaCCAuUu AcUuCaAL | |
| | AS | uUgAaGuAaAugg UgUuAaCc*A*g | |
| siAT-2 | S | G*g*UuAaCaCCAu UuAcUuCaAL | |
| | AS | u*U*gAaGuAaAugg UgUuAaCc*a*g | |

S and AS represent sense and antisense strands; upper case, and lower case letters indicate 2'-deoxy-2'-fluoro (2'-F), and 2'-O-methyl (2'-OMe) ribosugar modifications, respectively; * indicate PS linkage. L indicates the trivalent GalNAc ligand (structure above).

It is generally believed that, upon uptake, a fraction of the GalNAc-siRNAs reaches the cytoplasm and loads into the Argonaute protein in the RNA-induced silencing complex (RISC). Subsequently, the sense (or "passenger") strand of the siRNA is released, and the antisense (or "guide") strand facilitates sequence-specific enzymatic cleavage by guiding RISC to the complementary RNA, thereby decreasing protein expression in a highly targeted manner (Elbashir, S. M.; et al., *Nature,* 2001, 411, 494-98). Therefore it is expected that the GalNAc-siRNA conjugate, which possesses multiple functional groups or organic linkages of amide, ester, and/or ether between its GalNAc and siRNA components, will release siRNA in the cytoplasm by cleavage of the relevant chemical bond(s), either directly at the phosphate site or initiated at one or more amide sites. Indeed, as discussed above, targeted delivery of siRNA to the liver has been accomplished using a synthetic trivalent N-acetylgalactosamine (GalNAc) ligand covalently conjugated to a chemically modified small interfering RNA (siRNA). This strategy enabled safe and effective targeted delivery of siRNA to the liver mediated by the asialoglycoprotein receptor (ASGPR) located on the surface of hepatocytes, which triggers clathrin-mediated endocytosis to enable intracellular delivery of siRNA to elicit RNAi-mediated RNA silencing (Nair, J. K. et al. *Nucleic Acids Research,* 2017, 45(19), 10969-10977). Such intracellular delivery of siRNA generally involves cleavage of the covalent bond between the 3'-O of the sense strand and the linker moiety through cleavage of the P—O bond directly or triggered by cleavage of an amide bond in the spacer, as shown here:

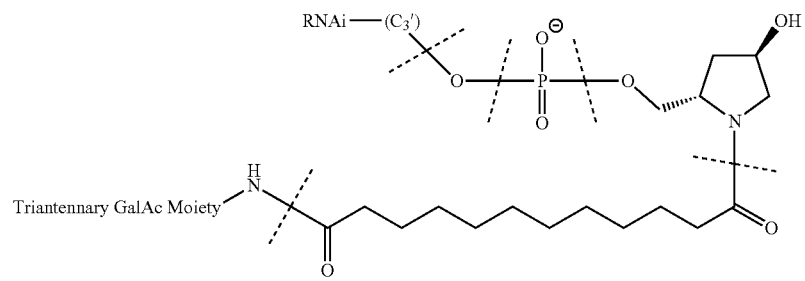

In the above example, the structure has at least two types of cleavable covalent bonds, an amide bond in the spacer and a phosphate ester bond in the linker, and can be cleaved at the positions indicated (dashed lines).

In an embodiment therefore, there is provided a GalNAc-siRNA conjugate with one or more heavy stable isotope(s) in the place of naturally-occurring isotope(s) in one or more amide group in the conjugate. In some embodiments, one or both amide oxygen(s) in the GalNAc-siRNA conjugate is enriched with $^{18}O$. Without wishing to be limited by theory, it is believed that $^{18}O$ enrichment in one or more amide oxygen(s) in the spacer may modify the rate of amide hydrolysis (chemically or enzymatically), which may in turn result in a rate change for intracellular release of RNAi intracellularly in cases where the amide cleavage leads to eventual cleavage of the phosphate linkage between the linker and the RNAi-moiety. In other embodiments, one or more oxygen(s) in the phosphate ester bond in the linker in the GalNAc-siRNA conjugate is partially or fully replaced with $^{18}O$. Without wishing to be limited by theory, it is believed that, when the $^{16}O$ on the right-side (and/or the left side) of the P-atom is replaced with $^{18}O$, the bond energy changes for both P—O and O—C, and in turn the hydrolysis rate at this site will be modified.

Non-limiting examples for $^{18}O$-isotope enrichment in a GalNAc-siRNA conjugate in accordance with some embodiments of the present technology are as follows, wherein the linker phosphate group is connected to RNAi at the 3'-position:

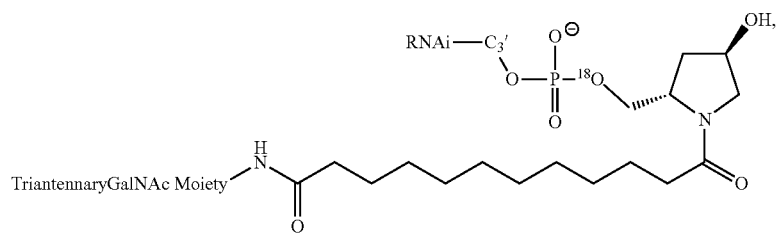

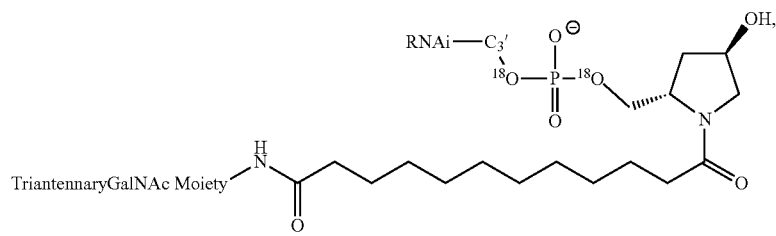

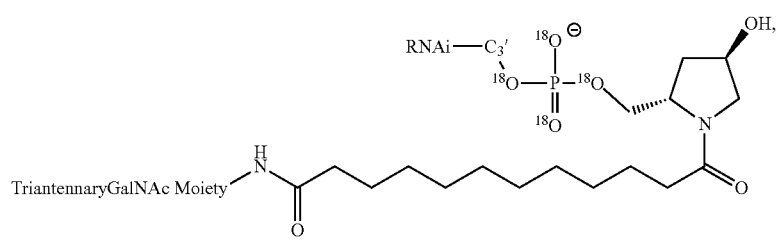

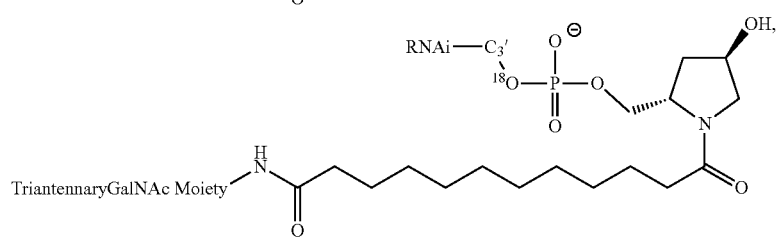

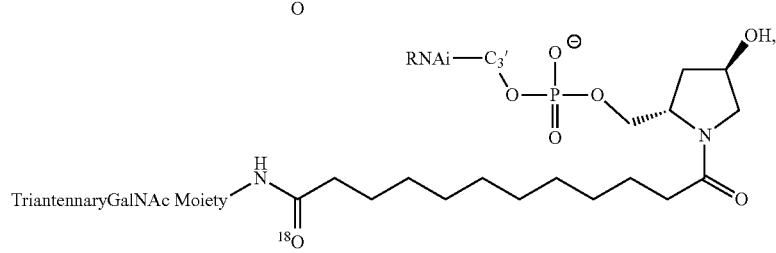

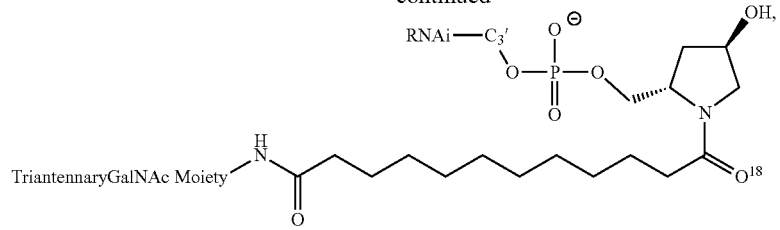
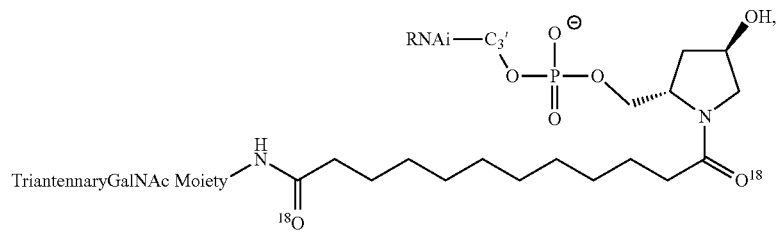
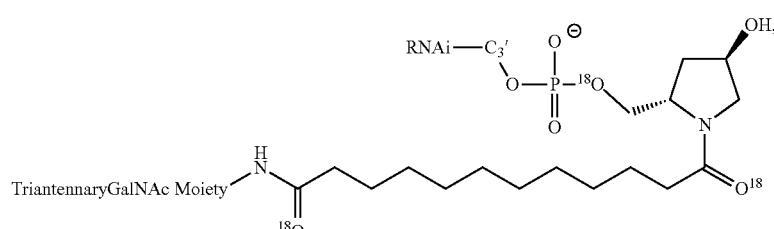
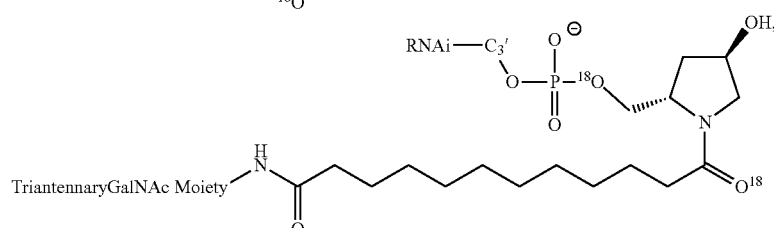
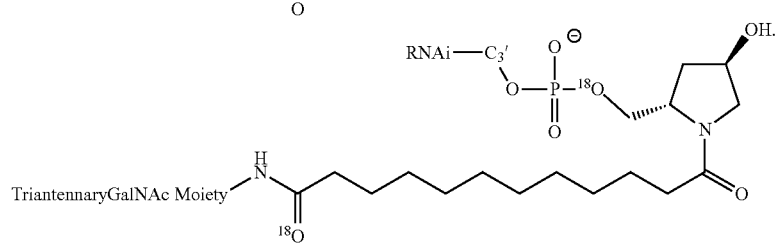
In other embodiments, the above examples are further extended to encompass various spacer lengths, as follows:
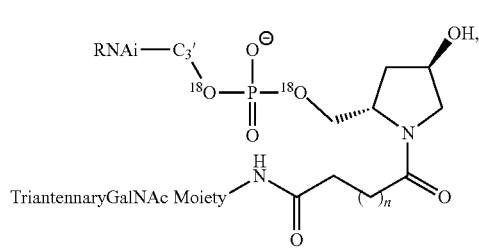
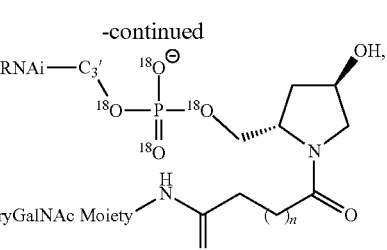
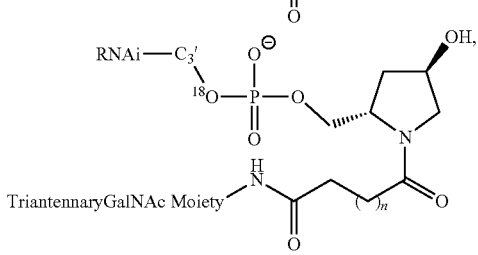
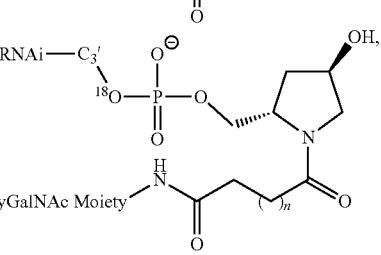

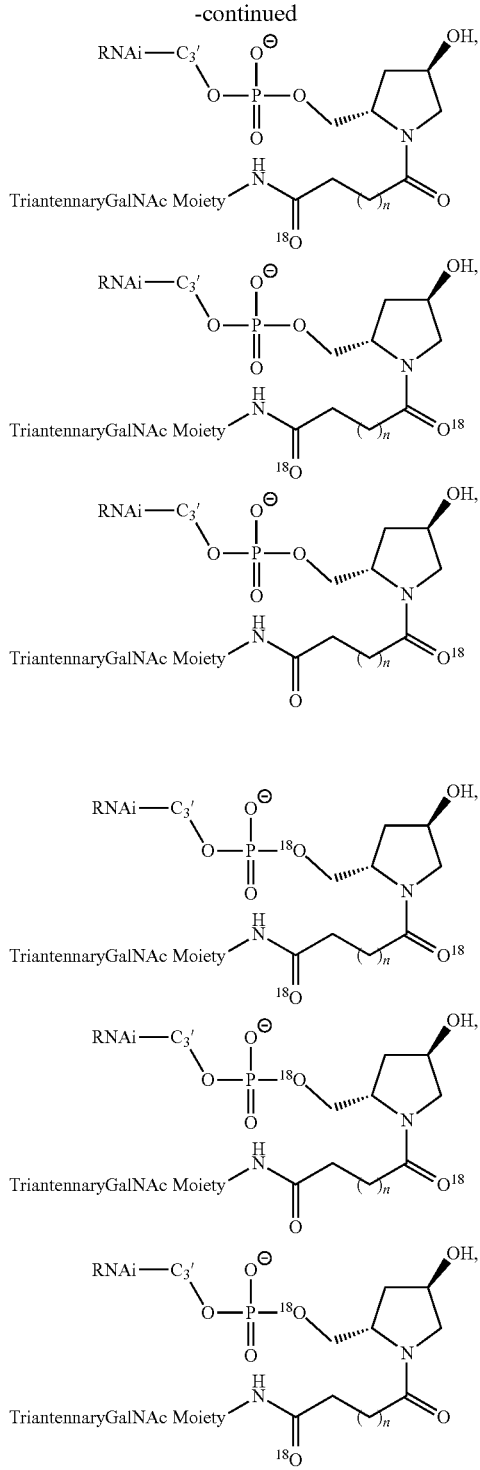

where n is an integer from 7 to 25. It should be understood that other combinations of stable isotope enrichment with $^{18}O$, or with combinations of $^{18}O$, $^{13}N$, and/or $^{13}C$ at positions of interest in a GalNAc-siRNA conjugate, are also contemplated and are meant to be encompassed herein.

In a particular embodiment, there are provided isotope-enriched compounds of Table 1, and pharmaceutically acceptable salts, esters, hydrates, chelates, and solvates thereof.

TABLE 1

Examples of isotope-enriched compounds of the present technology.

| Compound # | Structure |
|---|---|
| 1 | 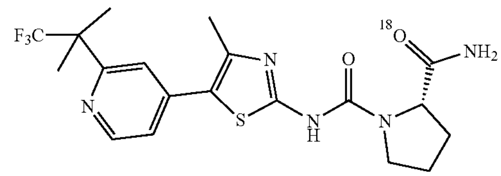 [SMILES: Cc1nc(NC(=O)N2CCC[C@H]2C(N)=O)sc1-c1ccnc(C(C)(C)C(F)(F)F)c1] |
| 2 | 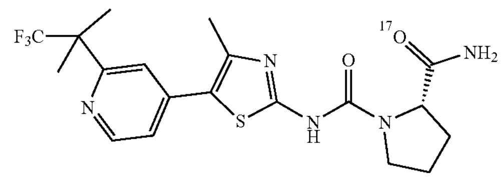 [SMILES: Cc1nc(NC(=O)N2CCC[C@H]2C(N)=O)sc1-c1ccnc(C(C)(C)C(F)(F)F)c1] |
| 3 | 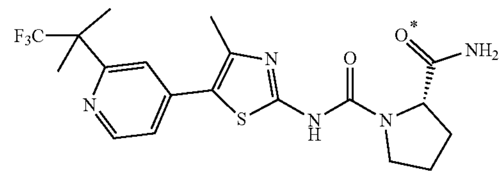 [SMILES: Cc1nc(NC(=O)N2CCC[C@H]2C(N)=O)sc1-c1ccnc(C(C)(C)C(F)(F)F)c1] |
| 4 | 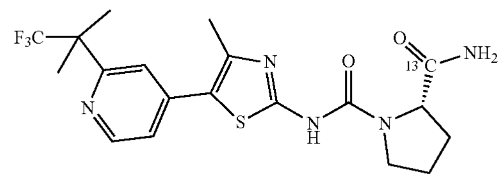 [SMILES: Cc1nc(NC(=O)N2CCC[C@H]2C(N)=O)sc1-c1ccnc(C(C)(C)C(F)(F)F)c1] |
| 5 | 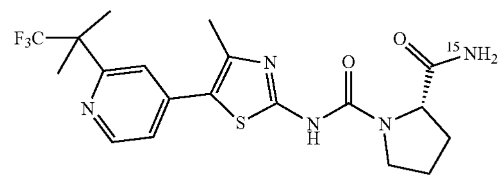 [SMILES: Cc1nc(NC(=O)N2CCC[C@H]2C(N)=O)sc1-c1ccnc(C(C)(C)C(F)(F)F)c1] |
| 6 | 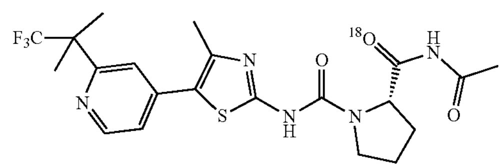 [SMILES: CC(=O)NC(=O)[C@@H]1CCCN1C(=O)Nc1nc(C)c(-c2ccnc(C(C)(C)C(F)(F)F)c2)s1] |
| 7 | 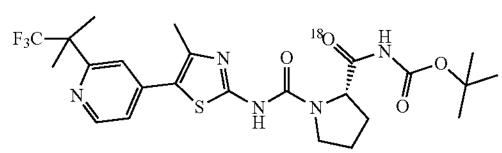 [SMILES: Cc1nc(NC(=O)N2CCC[C@H]2C(=O)NC(=O)OC(C)(C)C)sc1-c1ccnc(C(C)(C)C(F)(F)F)c1] |
| 8 | 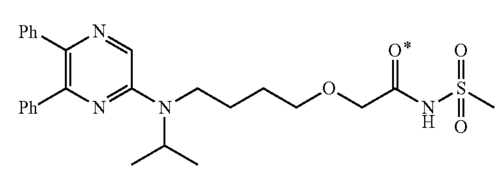 [SMILES: CC(C)N(CCCCOCC(=O)NS(C)(=O)=O)c1cnc(-c2ccccc2)c(-c2ccccc2)n1] |

TABLE 1-continued
Examples of isotope-enriched compounds of the present technology.
| Compound # | Structure |
|---|---|
| 9 | 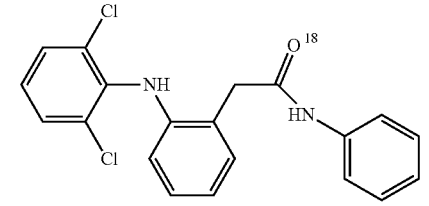 |
| 10 | 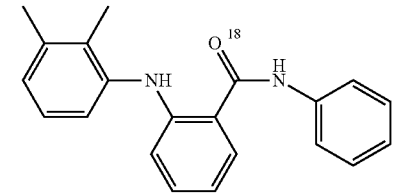 |
| 11 | 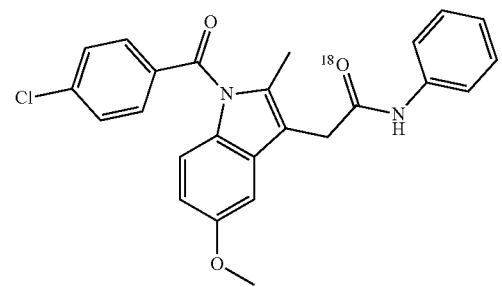 |
| 12 | 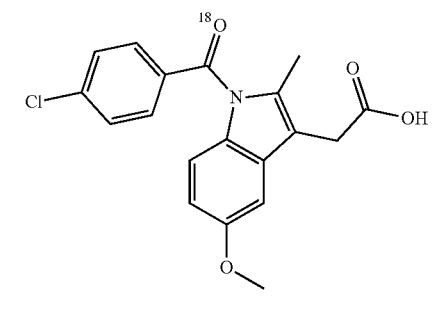 |
| 13 | 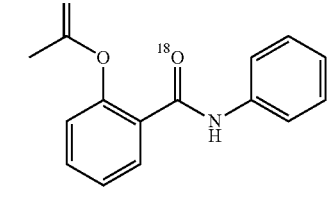 |
| 14 | 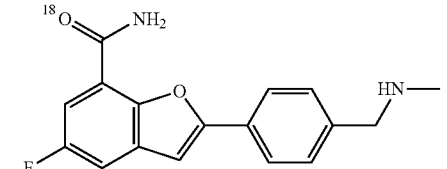 |
| 15 | 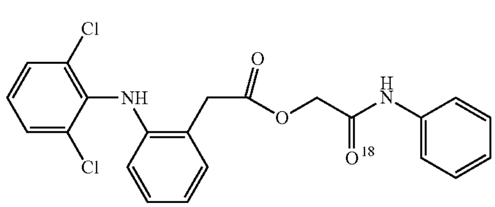 [SMILES: O=C(COC(=O)Cc1ccccc1Nc1c(Cl)cccc1Cl)Nc1ccccc1] |
| 16 | 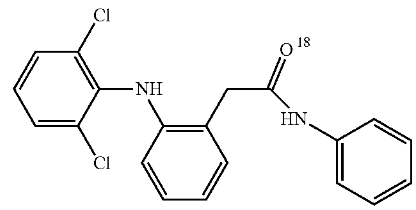 [SMILES: O=C(Cc1ccccc1Nc1c(Cl)cccc1Cl)Nc1ccccc1] |
| 17 | 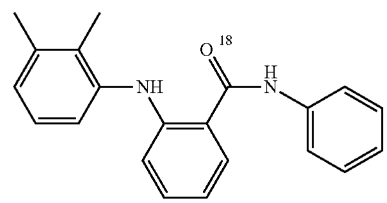 [SMILES: Cc1cccc(Nc2ccccc2C(=O)Nc2ccccc2)c1C] |
| 18 | 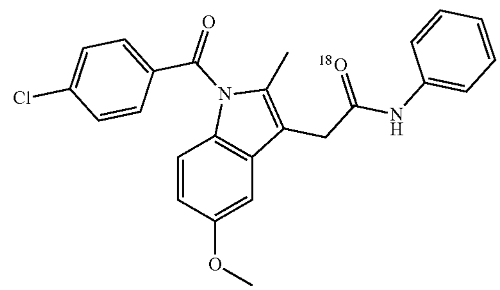 [SMILES: COc1ccc2c(c1)c(CC(=O)Nc1ccccc1)c(C)n2C(=O)c1ccc(Cl)cc1] |
| 19 | 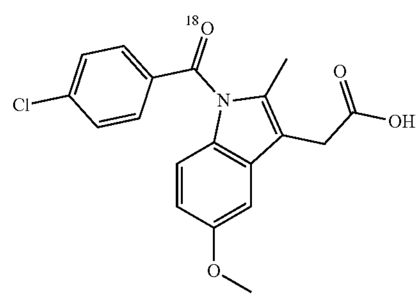 [SMILES: COc1ccc2c(c1)c(CC(=O)O)c(C)n2C(=O)c1ccc(Cl)cc1] |
| 20 | 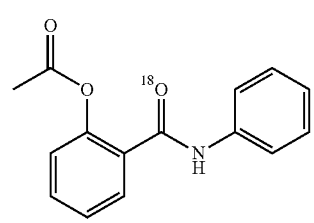 [SMILES: CC(=O)Oc1ccccc1C(=O)Nc1ccccc1] |
| 21 | 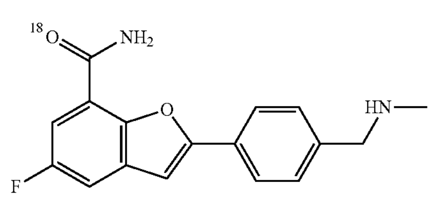 [SMILES: CNCc1ccc(-c2cc3cc(F)cc(C(N)=O)c3o2)cc1] |

TABLE 1-continued

Examples of isotope-enriched compounds of the present technology.

| Compound # | Structure |
|---|---|
| 22 | 5-fluoro-2-[4-(methylaminomethyl)phenyl]-1-benzofuran-7-carboxamide with $^{15}NH_2$ |
| 23 | 5-fluoro-2-[4-(methylaminomethyl)phenyl]-1-benzofuran-7-carboxamide with $^{13}C=O$ |
| 24 | 2-[4-(piperidin-3-yl)phenyl]-2H-indazole-7-carboxamide with $^{18}O$ |
| 25 | 2-[4-(piperidin-3-yl)phenyl]-2H-indazole-7-carboxamide with $^{15}NH_2$ |
| 26 | 2-[4-(piperidin-3-yl)phenyl]-2H-indazole-7-carboxamide with $^{13}C=O$ |
| 27 | (S)-2-[[4-[(3-fluorophenyl)methoxy]phenyl]methylamino]propanamide with $^{18}O$ |
| 28 | (S)-2-[[4-[(3-fluorophenyl)methoxy]phenyl]methylamino]propanamide with $^{13}C$ |
| 29 | (S)-2-[[4-[(3-fluorophenyl)methoxy]phenyl]methylamino]propanamide with $H_2{}^{15}N$ |
| 30 | 2-[4-[[2-(3-chlorophenyl)-6-(trifluoromethyl)pyrimidin-4-yl]amino]phenyl]acetamide with $^{18}O$ |
| 31 | 2-[4-[[2-(3-chlorophenyl)-6-(trifluoromethyl)pyrimidin-4-yl]amino]phenyl]acetamide with $^{13}C=O$ |
| 32 | 2-[4-[[2-(3-chlorophenyl)-6-(trifluoromethyl)pyrimidin-4-yl]amino]phenyl]acetamide with $^{15}N$ |
| 33 | Thr-Pro-Pro-Thr-NH$_2$ tetrapeptide with $^{18}O$ |
| 34 | Thr-Pro-Pro-Thr-NH$_2$ tetrapeptide with $^{13}C=O$ |

TABLE 1-continued

Examples of isotope-enriched compounds of the present technology.

| Compound # | Structure |
|---|---|
| 35 | (structure) |
| 36 | (structure) |
| 37 | (structure) |
| 38 | (structure) |
| 39 | (structure) |
| 40 | (structure) |
| 41 | 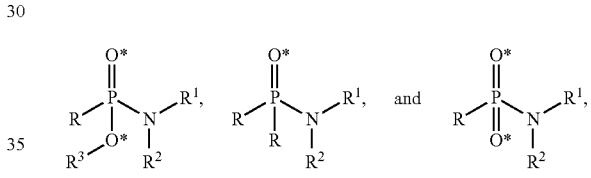 |

Many drugs and prodrugs have amide functional groups at critical sites of their structures, and many examples of isotope-enriched amide-containing drugs and prodrugs can be provided. It should be understood that the drugs and prodrugs comprising isotope-enriched amide functional groups of the present technology are not meant to be particularly limited.

Other types of amides are also within the scope of the invention, as illustrated below, as well as pharmaceutically acceptable salts, esters, hydrates, chelates, and/or solvates thereof. In another embodiment therefore, there are provided the following compounds, and pharmaceutically acceptable salts, esters, hydrates, chelates, and solvates thereof:

$$\underset{R^3}{\overset{O^*}{\underset{\|}{R-P-N}}}\underset{R^2}{\overset{R^1}{\underset{|}{\bigg\backslash}}}, \quad \underset{R}{\overset{O^*}{\underset{\|}{R-P-N}}}\underset{R^2}{\overset{R^1}{\underset{|}{\bigg\backslash}}}, \quad \text{and} \quad \underset{O^*}{\overset{O^*}{\underset{\|}{R-P-N}}}\underset{R^2}{\overset{R^1}{\underset{|}{\bigg\backslash}}},$$

where: O* is an amide oxygen atom enriched with a stable heavy oxygen-isotope ($^{17}$O and/or $^{18}$O); R, $R^1$, and $R^2$ are as defined above; and the isotope-enriched structures are present in, or provide O*-enriched drug and/or prodrug compounds containing at least one amide-linkage, such as without limitation a phosphonamide, a phosphoramide, and/or a sulfonamide linkage.

In a second broad aspect, there are provided pharmaceutical compositions comprising an isotope-enriched compound described herein, or a pharmaceutically acceptable salt, ester, hydrate, chelate, or solvate thereof, and a pharmaceutically acceptable carrier.

In a third broad aspect, there are provided methods of modulating or modifying the pharmacokinetic profile of a drug or prodrug by replacing one or more of the three naturally-occurring atoms ((C(=O)—N)) in an amide functional group or linkage with one or more heavy stable isotope atom(s).

In one embodiment, an isotope-enriched compound described herein (e.g., a compound of Formulae I, II or III, a compound of Table 1), and/or a pharmaceutical composition thereof, is used in a subject to modulate a metabolic pathway, reduce drug metabolism, modulate pharmacokinetic profile, and/or improve or increase therapeutic effect of a drug or prodrug in a subject, as compared to use of the compound having only atoms of natural isotope abundance (i.e., non-isotope-enriched compound). In some embodiments, isotope-enriched compounds and pharmaceutical compositions provided herein are used in a subject to reduce therapeutic toxicity and/or adverse effects of a compound, increase tolerability of a compound, and/or improve or increase therapeutic or prophylactic effect of a compound in a subject, as compared to use of the compound having only isotopes of natural abundance (i.e., non-isotope-enriched compound). In some embodiments, isotope-enriched compounds and pharmaceutical compositions provided herein are used in a subject to improve biodistribution and/or enhance therapeutic and/or prophylactic effect of a compound in a subject, as compared to use of the compound having only isotopes of natural abundance (i.e., the non-isotope-enriched compound).

In an embodiment, there is provided a method of modulating the metabolism or the pharmacokinetic profile of an amide-bond containing (i.e., an amide functional group containing) compound in a subject, comprising administering to the subject an isotope-enriched compound and/or a pharmaceutical composition as described herein, wherein the metabolism or the pharmacokinetic profile of the isotope-enriched amide-bond containing compound is modulated compared to administration of the same compound having only isotopes of natural abundance (i.e., the non-isotope-enriched compound). In some embodiments, there is provided a method of reducing the metabolism of a compound, reducing a compound's therapeutic toxicity, reducing a compound's adverse effects, increasing tolerability of a compound, improving biodistribution of a compound, and/or increasing the therapeutic or prophylactic effect of a compound in a subject, the method comprising administering to the subject an isotope-enriched compound or pharmaceutical composition as described herein, wherein the isotope-enriched compound's metabolism is reduced, therapeutic toxicity is reduced, adverse effects are reduced, tolerability is increased, biodistribution is improved, and/or therapeutic or prophylactic effect is increased as compared to administration of the compound having only isotopes of natural abundance (i.e., the non-isotope-enriched compound).

In a fourth broad aspect, there is provided a method of treating a disease state or condition associated with activity of phosphoinositide 3-kinase in a subject in need thereof, the method comprising administering to the subject a therapeutically effective amount of an isotope-enriched compound and/or a pharmaceutical composition as described herein. Any disease or condition ameliorated by inhibition of phosphoinositide 3-kinase (referred to herein as a "PI3K mediated disease") may be treated using compounds and compositions provided herein. In some embodiments, a phosphoinositide 3-kinase (PI3K) mediated disease is a PI3K alpha mediated disease (or disease mediated by overexpression or amplification of PI3K alpha, somatic mutation of PI3K or germline mutations or somatic mutation of PTEN or mutations and translocation of p85alpha that serve to upregulate the p85-p110 complex), especially such disorders that respond in a beneficial way to the inhibition of a PI3 kinase, especially inhibition of PI3K alpha or a mutant form thereof.

In some embodiments, the disease state or condition to be treated is a cellular proliferative disease such as tumor and/or cancerous cell growth mediated by PI3K. Diseases may include those showing overexpression or amplification of PI3K alpha, somatic mutation of PIK3CA or germline mutations or somatic mutation of PTEN or mutations and translocation of p85alpha that serve to up-regulate the p85-p110 complex. In particular, the compounds are useful in the treatment of human or animal (e.g., murine) cancers, including, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and Waldenstroem disease. In one embodiment, the disease state or condition to be treated is breast cancer. In some such embodiments, the disease state or condition to be treated is hormone receptor positive (HR$^+$), human epidermal growth factor receptor negative (HER2$^-$) breast cancer. In a further embodiment, the disease state or condition to be treated is HR$^+$, HER2$^-$, and PIK3CA mutated breast cancer.

In other embodiments, the PI3K mediated condition or disorder is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In some embodiments, the disease state or condition is a solid tumor or a cancer or proliferative disorder such as, without limitation, breast cancer, melanoma, colon cancer, colorectal adenoma, pancreatic cancer, prostate cancer, lung cancer, leukemia, a brain tumor, lymphoma, ovarian cancer, Kaposi's sarcoma, rectal cancer, renal cell carcinoma, glioblastoma, non-small cell lung cancer, head and neck cancer, multiple myeloma, esophageal cancer, gastric cancer, gastrointestinal stromal tumor, or uveal melanoma. In some embodiments, therefore, there is provided a method of treating a cancer, a solid tumor or a proliferative disease comprising administering to the subject a therapeutically effective amount of an isotope-enriched compound and/or a pharmaceutical composition as described herein, such that the cancer, solid tumor or proliferative disease is treated.

In another broad aspect, there are provided kits comprising one or more isotope-enriched compound or pharmaceutical composition described herein. A kit may further comprise one or more additional therapeutic agents and/or instructions, for example, instructions for using the kit to treat a subject having disease states or conditions the same as or similar to that treated by the parent (i.e., not isotope-enriched) compounds.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Definitions

Figure 1A:
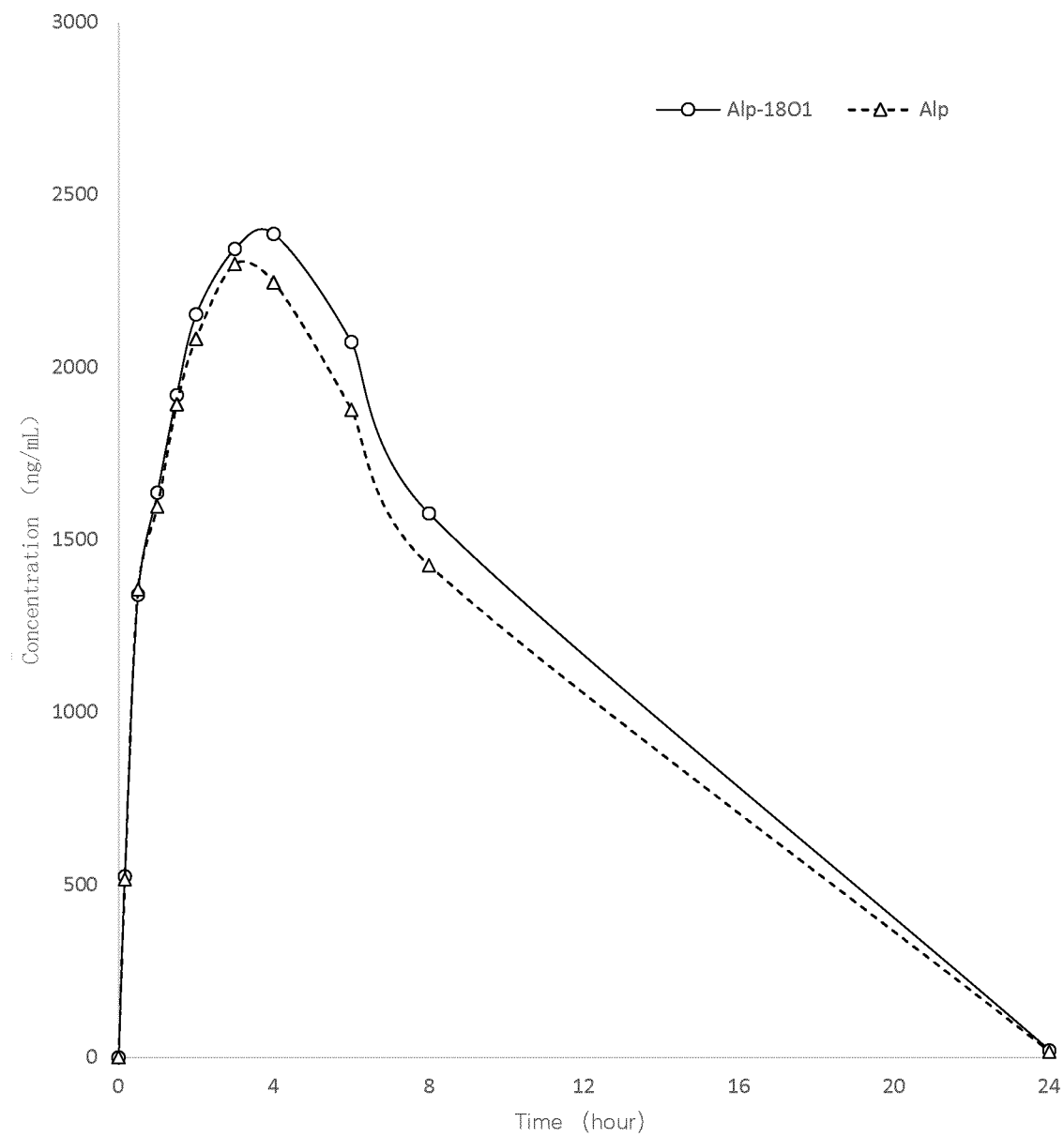
FIGS. 1a and 1b show plasma drug concentration-time curves from Alpelisib (dashed line) and Alpelisib-$^{18}O_1$ (solid line) in SD rats with oral administration of the same dose of Alpelisib and Alpelisib-$^{18}O_1$: (1a) at a dose of 2.5 mg/kg, and (1b) at a dose of 0.322 mg/kg.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used herein, the term "atom of natural abundance" refers to an atom of natural isotope abundance, normally having the isotopic composition of the atoms close to Earth's atmosphere. However, it should be understood that naturally occurring compounds may have slight variations in the isotopic composition of various atoms. By way of example, the term "oxygen of natural abundance" refers to an oxygen atom of natural isotope abundance, normally having the isotopic composition of oxygen atoms close to the Earth's atmosphere: $^{16}O$, 99.759%; $^{17}O$, 0.037%; and $^{18}O$, 0.204%. However, it should be understood that naturally occurring compounds may have slight variations in the isotopic composition of oxygen atoms.

The terms "heavy oxygen atom", "heavy oxygen isotope", "stable heavy oxygen", "O" and "0" are used interchangeably to refer to stable oxygen atoms of $^{17}O$ and/or $^{18}O$, with exclusion of any radioactive and non-naturally occurring heavy isotope. $^{17}O$ and $^{18}O$ are present naturally but at very low ratios compared to the predominant isotope $^{16}O$. The terms "heavy carbon isotope", "stable heavy carbon isotope", "carbon-13", "$^{13}C$", and "C" are used interchangeably herein to refer to the $^{13}C$ isotope. Similarly, the terms "heavy nitrogen isotope", "stable heavy nitrogen isotope", "nitrogen-15", "$^{15}N$", and "*N" are used interchangeably herein to refer to the $^{15}N$ isotope.

As used herein, the terms "oxygen atom enriched with stable heavy oxygen isotope", "stable heavy oxygen-enriched", "heavy oxygen enriched", "*O-enriched" and "O*-enriched" are used interchangeably to refer to an oxygen atom which is not in its natural isotopic composition and has a higher level of stable heavy oxygen isotope than found in the naturally occurring isotopic composition. The terms "heavy oxygen-enriched", "stable heavy oxygen-enriched", "*O-enriched", and "O*-enriched" are used interchangeably to refer to an oxygen atom at a particular site of a compound being enriched with a stable heavy oxygen isotope, either with $^{17}O$, or $^{18}O$, or a mixture of $^{17}O$ and $^{18}O$, as described herein. Similarly, reference to carbon or nitrogen atom enriched with stable heavy atom isotope, $^{13}C$- or $^{15}N$-enriched respectively, refers to carbon or nitrogen atom that is not in natural isotopic composition, where the fraction of heavy isotope, $^{13}C$ or $^{15}N$, in the compound is higher than found in naturally occurring carbon or nitrogen respectively.

Isotopic enrichment is a process by which the relative abundance of the isotopes of a given element are altered, thus producing a form of the element that has been enriched (i.e., increased) in one particular isotope and reduced or depleted in its other isotopic forms. As used herein, an "heavy isotope-enriched" compound or derivative refers to a compound in which a specific isotopic form has been increased at a specific position or site of an amide linkage, i.e., oxygen-17 or oxygen-18, or both oxygen-17 and oxygen-18, and/or carbon-13, and/or nitrogen-15, has been enriched (i.e., increased).

For carbon and nitrogen, the most abundant heavy isotopes are $^{13}C$ and $^{15}N$, at levels of 0.0107 and 0.00364 in mole fraction, as compared to levels of the most abundant isotopes $^{12}C$ of 0.9893 and $^{14}N$ of 0.99636 in mole fraction, respectively. Under normal conditions, oxygen-18 ($^{18}O$) and oxygen-17 ($^{17}O$) are at levels of 0.00204 and 0.00037 respectively, with oxygen-16 ($^{16}O$), the most abundant oxygen isotope, at a level of 0.99757, all in mole fractions. As such, the ratio of $^{18}O$ to $^{16}O$ is approximately 0.2%.

As used herein, an "isotope-enriched" compound or derivative possesses a level of an isotopic form of an atom or element (e.g., $^{18}O$), that is higher than the natural abundance of that form (e.g., $^{16}O$). The level of isotope-enrichment will vary depending on the natural abundance of a specific isotopic form. As used herein, the expression "level of isotope-enrichment" means the amount or percentage of the compound that includes an isotopic form of an atom or element in place of the isotope of highest natural abundance. The terms "level of enrichment" and "%-enriched" are used interchangeably to refer to the amount or mole percentage of the compound that includes an isotopic form of an atom or element. For example, "95% $^{18}$O-enriched" means that 95 out of 100 (95/100) molecules have $^{18}$O-isotope, and 5/100 do not have $^{18}$O but instead have other isotopic forms of oxygen ($^{17}$O and/or $^{16}$O). Similarly, 95% $^{18}$O-enriched at a certain position/atom within the compound's structure means that 95/100 molecules have $^{18}$O at that position/atom in the compound, whereas the other 5/100 have other isotopic forms of oxygen ($^{17}$O and/or $^{16}$O) at that same position/atom. In some embodiments, the level of isotope-enrichment for a compound, or for an element in a compound, may be from about 2 to about 100 molar percent (%), e.g., about 2%, about 5%, about 17%, about 30%, about 51%, about 83%, about 90%, about 95%, about 98%, greater than about 98%, about 99%, or 100%. In one embodiment, the level of isotope-enrichment in an isotope-enriched compound of the invention (e.g., a compound of any of Formulae I to III, or a compound in Table 1, etc.) is about 5% or higher, or about 10% or higher. In another embodiment, the level of isotope-enrichment in an isotope-enriched compound of the invention (e.g., a compound of any of Formulae I to III, and compounds described herein) is about 20% or higher, or about 50% or higher. In yet another embodiment, the level of isotope-enrichment in an isotope-enriched compound of the invention (e.g., a compound of any of Formulae I to III, and compounds described herein) is about 75% or higher, or about 90% or higher. In still another embodiment, the level of isotope-enrichment in an isotope-enriched compound of the invention (e.g., a compound of any of Formulae I to III, and compounds described herein) is about 90% or higher, about 91% or higher, about 92% or higher, about 93% or higher, about 94% or higher, about 95% or higher, about 96% or higher, about 97% or higher, about 98% or higher, about 99% or higher or 100%. In some embodiments, the level of isotope-enrichment for a compound is determined using mass spectrometry. It should be understood that the level of isotope-enrichment for a particular compound, or a particular oxygen isotope of a compound, will be selected based on several properties of the compound such as its chemical, pharmacokinetic, and therapeutic profiles, with the aim of improving the compound's therapeutic or prophylactic efficacy, therapeutic bio-distribution, bioavailability, metabolism, stability, and/or pharmacokinetic profile, and/or reducing the compound's adverse effects.

As used herein, a "non-isotope enriched" compound is a compound in which all the atoms or elements in the compound are isotopes of natural abundance, i.e., all the atoms or elements have the atomic mass most abundantly found in nature. This is in contrast to an isotope-enriched compound in which one or more element is enriched for one or more specific isotopic form that is not the isotope of natural abundance. Non-isotope enriched compounds are excluded from compounds of the present invention provided herein.

As used herein, the terms "Compounds of the present invention", "Compounds of the invention", and equivalent expressions refer to isotope-enriched compounds provided herein as being useful for at least one purpose described herein, e.g., those encompassed by structural Formulae such as Formulae I to III and including specific compounds described herein, as well as their pharmaceutically acceptable salts, esters, chelates, hydrates, and/or solvates.

As used herein, "isotopic effect" refers to the effect of a stable heavy isotope (which replaces an isotope of natural abundance) on the rate of amide-bond cleavage. Without wishing to be limited by theory, a heavy isotope may alter the strength of an amide-bond due to its increased mass and thus cause a decrease in the reaction rate of amide-bond cleavage. For amide hydrolysis, the key rate-determining step of hydrolysis is generally the attack of a water molecule on the carbon atom in the amide group, which is in a planar structure. The n-bond in the original carbon-oxygen double bond breaks gradually with the approach of the oxygen atom in water molecules, thus forming a four-coordination intermediate. If the firmness or strength of the carbon-oxygen double bond is changed, then the rate of hydrolysis may be changed accordingly. Introduction of heavy stable isotopes may therefore slow down the hydrolysis of an amide to a carboxylic acid. This change in the rate of amide-bond cleavage can modify the pharmacokinetic profile of amide-bond containing drugs and prodrugs, and thus modulate the therapeutic, prophylactic, and/or adverse effect of the drugs and prodrugs. Since the carboxylic amide center involves three atoms, oxygen, carbon, and nitrogen, stable heavy isotopes of oxygen and/or carbon and/or nitrogen could potentially have an isotopic effect on amide-bond containing drugs and prodrugs.

Not to be limited by theory, the two heavy oxygen isotopes, namely $^{18}$O and $^{17}$O, can have different isotopic effects regarding cleavage of the amide bond, such as the rate of hydrolysis reaction. Since $^{18}$O has an atomic weight of 18-Dalton, it may in some cases have higher isotopic effect than $^{17}$O does (atomic weight of 17-Dalton) due to its higher mass. Enrichment can be selected with $^{18}$O or $^{17}$O, or a mixture of $^{18}$O and $^{17}$O at various ratios to achieve the desired biological and pharmaceutical effect(s). Similarly, heavy isotope $^{13}$C and/or $^{15}$N enrichment can be selected to achieve desired biological and pharmaceutical effect(s) of the isotope-enriched compounds. Like $^{17}$O, $^{13}$C may in some cases have lower isotopic effect than $^{18}$O due to the smaller change in molecular weight compared to the isotope of natural abundance (the molecular weight increment from $^{12}$C to $^{13}$C is 8.3%; 6.25% from $^{16}$O to $^{17}$O; and 12.5% from $^{16}$O to $^{18}$O).

An isotope-enriched compound, as described herein, can be enriched isotopically with one or more isotopes of the same element, or with isotopes of one or more elements.

As used herein, a "drug" or a "prodrug", or a "parent compound", refers to a compound of natural isotope abundance at the amide site of interest. The present technology provides compounds, compositions, and methods for preparation and use of such compounds in "heavy isotope-enriched" form, in order to modulate or improve the pharmaceutical profile and/or therapeutic efficacy of the parent compound. In some embodiments, a "drug" or a "prodrug", or a "parent compound", refers to a compound of natural oxygen, carbon and/or nitrogen isotope abundance at the respective amide-oxygen, carbon and/or nitrogen site of interest; the present technology thus provides compounds, compositions, and methods for preparation and use of such compounds in "heavy oxygen, carbon and/or nitrogen-enriched" form, in order to modulate or improve the pharmaceutical profile and/or therapeutic efficacy of the parent compound.

As used herein, an "organic moiety" or "organic fragment" refers to a group of atoms which become part of the entire structure of an isotope-enriched compound. The organic moiety, the amide linkage or functional group, and a protecting or substituent group (if present) are generally linked together with covalent bonds, forming the structure of an isotope-enriched compound.

In one embodiment, an isotope-enriched compound can be further substituted with one or more substituting groups when such a substitution is available. In some embodiments, a substituted form of a compound is a prodrug; in such embodiments, the substituent can be cleaved, or the compound can be otherwise converted, to release the active component or the drug compound from the prodrug form after being administered to a subject.

As used herein, the term "administration" or "administered" refers to delivering a compound to a subject, including all the means of dosing and drug delivery known in the art.

As used herein, the words "comprising" (and any form of comprising, such as "comprise" and "comprises"), "having" (and any form of having, such as "have" and "has"), "including" (and any form of including, such as "include" and "includes") and "containing" (and any form of containing, such as "contain" and "contains"), are inclusive or open-ended and do not exclude additional, unrecited elements or process steps.

The term "about" is used herein to indicate that a value includes an inherent variation of error for the device or the method being employed to determine the value.

The term "derivative" as used herein refers to a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "substituted" or "with substitution" refers to a compound or a moiety having at least one (1) substituent group. The term "unsubstituted" or "without substitution" refers to a compound or a moiety having no other substituent group except that the unidentified valence is chemically saturated with hydrogen atoms.

As used herein, a "substituent" or a "substituent group" refers to a group selected from halogen (F, Cl, Br, or I), hydroxy, sulfhydryl, amino, nitro, carbonyl, carboxyl, alkyl, alkoxyl, alkylamino, aryl, aryloxyl, arylamino, acyl, thionyl, sulfonyl, phosphonyl, and other organic moiety as used and accepted in general organic chemistry.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal to or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal to or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of structures of bicyclic ring systems are norbornane, bicyclo[2.2.1]heptane, bicyclo[2.2.2]octane and bicyclo[3.2.1]octane.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal to or less than 8 carbon atoms in their ring structure.

The terms "aryl" and "aryl ring" refer to aromatic groups having "4n+2" π (pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-

$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "4n+2".pi.(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to a heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like.

The term heterocycle includes both unsubstituted heterocyclic groups and substituted heterocyclic groups.

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein mean an amine group having respectively one and at least two $C_1$-$C_6$alkyl groups attached thereto. The terms "arylamino" and "diarylamino" include groups wherein the nitrogen is bound to at least one or two aryl groups, respectively. The terms "amide" or "aminocarbonyl" include compounds or moieties which contain a nitrogen atom which is bound to the carbon of a carbonyl or a thiocarbonyl group. The term "acylamino" refers to an amino group directly attached to an acyl group as defined herein.

The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The terms "alkoxy" or "lower alkoxy" as used herein mean an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups, and the like. The term "alkoxy" includes both unsubstituted or substituted alkoxy groups, etc., as well as perhalogenated alkyloxy groups.

The terms "carbonyl" or "carboxy" include compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_6$alkyl, $C_1$-$C_6$alkenyl, $C_1$-$C_6$alkynyl, e.g., acetyl), a cycloalkyl group ($C_3$-$C_8$cycloalkyl), a heterocyclic group ($C_3$-$C_5$ heterocycloalkyl and $C_5$-$C_6$ heteroaryl), an aromatic group ($C_6$ aryl, e.g., benzoyl), and the like. Acyl groups may be unsubstituted or substituted acyl groups (e.g., salicyloyl).

The term "solvate" refers to a physical association of a compound with one or more solvents, whether organic or inorganic. This physical association includes hydrogen bonding. In certain instances, a solvate will be capable of isolation, for example when one or more solvents are incorporated in the crystal lattice of a crystalline solid. "Solvate" encompasses both solution-phase and isolable solvates. Exemplary solvates include, without limitation, hydrates, ethanolates, methanolates, hemiethanolates, and the like.

A "pharmaceutically acceptable salt" of a compound means a salt of a compound that is pharmaceutically acceptable. Desirable are salts of a compound that retain or improve the biological effectiveness and properties of the free acids and bases of the same compound as defined herein or that take advantage of an intrinsically basic, acidic or charged functionality in the compound and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, p-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the starting compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a starting compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts" also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

As used herein the term "effective amount" refers to the amount or dose of a therapeutic agent, such as a compound, upon single or multiple dose administration to a subject, which provides the desired therapeutic, prophylactic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

"Pharmaceutically acceptable" refers to drugs, medicaments, inert ingredients etc., which the term describes, suitable for use in contact with the cells or tissues of humans and animals without undue toxicity, incompatibility, instability, irritation, allergic response, and the like, commensurate with a reasonable benefit/risk ratio. It generally refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, vehicle or carrier with which a compound is administered. The terms "Pharmaceutically acceptable vehicle" and "Pharmaceutically acceptable carrier" are used interchangeably herein.

"Pharmaceutical composition" refers to a composition comprising a compound as described herein and at least one component comprising a pharmaceutically acceptable carrier, diluent, adjuvant, excipient, or vehicle, such as a preserving agent, a filler, a disintegrating agent, a wetting agent, an emulsifying agent, a suspending agent, a sweetening agent, a flavoring agent, a perfuming agent, an antibacterial agent, an antifungal agent, a lubricating agent, a dispensing agent, and the like, depending on the nature of the mode of administration and dosage forms. "Preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder. In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In some embodiments, "treating" or "treatment" refers to improving the quality of life or reducing the symptoms or side effects of a disease in a subject in need thereof. "Therapeutically effective amount" means the amount of a compound that, when administered to a subject for treating or preventing a disease, is sufficient to effect such treatment or prevention of the disease. The "therapeutically effective amount" will vary depending on the compound, the disease and its severity, and the age, weight, etc., of the subject having the disease to be treated or prevented. As used herein, the term "therapeutically effective amount" refers to an amount of a compound or composition sufficient to prevent, treat, inhibit, reduce, ameliorate or eliminate one or more causes, symptoms, or complications of a disease such as a cancer.

The term "subject" includes animals, including mammals and humans, particularly humans. Non-limiting examples of subjects include humans, monkeys, cows, rabbits, sheep, goats, pigs, dogs, cats, rats, mice, and transgenic species thereof.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the bio-distribution (e.g., to allow agents which would not typically enter the reactive site of a protease) or the pharmacokinetics for a particular agent. A wide variety of groups have been used to modify compounds to form prodrugs, for example, esters, ethers, phosphates, etc. When a prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the active form.

The term "ester" refers to compounds that can be represented by the formula RCOOR (carboxylic ester) or the formula $RSO_3R'$ (sulfonate ester), usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated and N-alkylated amino acids, as well as amino acids having nitrogen or oxygen-containing side chains (such as Lys, Cys, or Ser) in which the nitrogen or oxygen atom has been acylated or alkylated. Amino acids may be pure L or D isomers or mixtures of L and D isomers, including (but not limited to) racemic mixtures.

The term "natural amino acid" and equivalent expressions refer to L-amino acids commonly found in naturally-occurring proteins. Examples of natural amino acids include, without limitation, alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-Ala), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH2-Phe), 2-aminopimelic acid (Apm), biphenylalanine (Bip), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-Cl-2-Phe), 3,4-difluorophenylalanine (3,4-F2-Phe), 3,5-diiodotyrosine (3,5-I2-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-NO2-Phe), 3-nitrotyrosine (3-NO2-Tyr), norleucine (Nle), norvaline (Nva), ornithine (Orn), ortho-phosphotyrosine (H2PO3-Tyr), octahydroindole-2-carboxylic acid (Oic), penicillamine (Pen), pentafluorophenylalanine (F5-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

For isotope-enriched compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc,) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds provided herein include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds provided herein include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

In some embodiments, the compound of the invention is isotope-enriched alpelisib, e.g., $^{13}C_1$-alpelisib, $^{18}O_1$-alpelisib, $^{17}O_1$-alpelisib, $^{13}C_1{}^{18}O_1$-alpelisib and/or $^{13}C_1{}^{17}O_1$-alpelisib. Alpelisib is an inhibitor of phosphatidylinositol-3-kinase (PI3K) with inhibitory activity predominantly against PI3Kα. Gain-of-function mutations in the gene encoding the catalytic α-subunit of PI3K (PIK3CA) lead to activation of PI3Kα and Akt-signaling, cellular transformation and the generation of tumors in in vitro and in vivo models. In breast cancer cell lines, alpelisib inhibited the phosphorylation of PI3K downstream targets, including Akt and showed activity in cell lines harboring a PIK3CA mutation. In vivo, alpelisib inhibited the PI3K/Akt signaling pathway and reduced tumor growth in xenograft models, including models of breast cancer. PI3K inhibition by alpelisib treatment has been shown to induce an increase in estrogen receptor (ER) transcription in breast cancer cells. A combination of alpelisib and fulvestrant demonstrated increased antitumor activity compared to either treatment alone in xenograft models derived from ER-positive, PIK3CA mutated breast cancer cell lines. Alpelisib was approved by the FDA as Piqray™, e.g. for use in combination with fulvestrant for treatment of postmenopausal women and men with HR-positive, HER2-negative, PIK3CA-mutated, advanced or metastatic breast cancer.

In a particular embodiment, the compound of the invention is $^{18}O_1$-alpelisib (also referred to herein as Alpelisib-$^{18}O_1$). $^{18}O_1$-Alpelisib is a stable isotopic form of alpelisib, with the oxygen atom at the prolinamide position enriched with oxygen-18, or $^{18}O$. The chemical name of the compound is (2S)—N$^1$-[4-Methyl-5-[2-(2,2,2-trifluoro-1,1-dimethylethyl)-4-pyridinyl]-2-thiazolyl]-1,2-pyrrolidinedicarboxamide. The compound has the structure shown here:

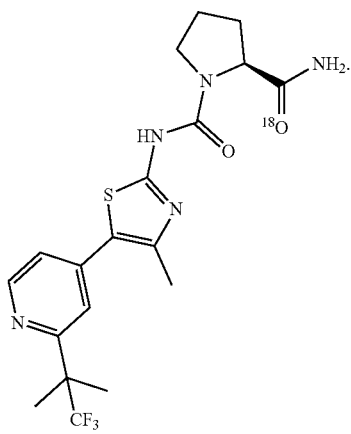 [SMILES: Cc1nc(NC(=O)N2CCC[C@H]2C(N)=[18O])sc1-c1ccnc(C(C)(C)C(F)(F)F)c1]

In some embodiments, isotope-enriched alpelisib, e.g., $^{18}O_1$-alpelisib, has a level of isotope-enrichment of about 90% or higher, about 91% or higher, about 92% or higher, about 93% or higher, about 94% or higher, about 95% or higher, about 96% or higher, about 97% or higher, about 98% or higher, about 99% or higher or 100%. In one embodiment, there is provided $^{18}O_1$-alpelisib having 95% or greater $^{18}O$-isotope enrichment. In an embodiment, there is provided $^{18}O_1$-alpelisib having 94% or greater $^{18}O$-isotope enrichment. In an embodiment, the level of isotope enrichment is determined using mass spectrometry.

Figure 5:
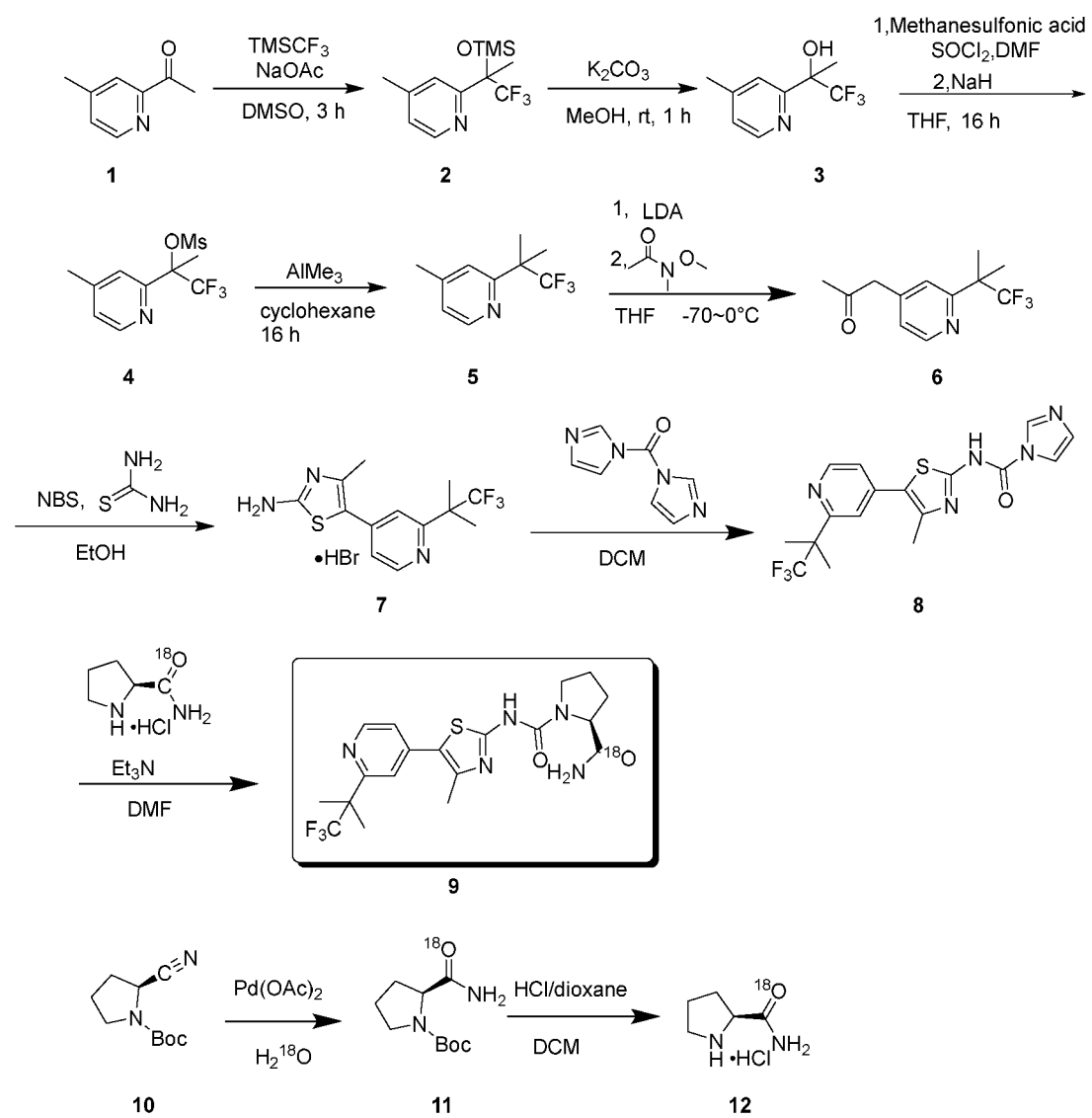
FIG. 5 shows an example of a chemical synthesis pathway for $^{18}O_1$-Alpelisib.

In some embodiments, Alpelisib-$^{18}O_1$ is prepared using $H_2{}^{18}O$, or $^{18}O$-water, as the source of $^{18}O$. Alpelisib-$^{18}O_1$ can be prepared using, for example and without limitation, the route of synthesis shown in FIG. 5. This route of synthesis ensures that only the isotopically enriched $^{18}O$-water will be incorporated in the carboxamide-substituted pyrrolidine ring of alpelisib. In this case, the level of isotope enrichment in the compound can be equivalent to, or slightly below, that of the $^{18}O$-water. For example, $^{18}O$-water typically contains a certain level of $^{16}O$ and $^{17}O$, for example about 1-1.5% of $^{16}O$ and a similar or even higher level of $^{17}O$, which will be carried into the $^{18}O$-Alpelisib using this method. The resultant Alpelisib-$^{18}O_1$ would therefore have, for example, ≥95% (+0.5%) $^{18}O$-isotope enrichment, ≥96% (±0.5%)$^{18}O$-isotope enrichment, ≥97% (+0.5%) $^{18}O$-isotope enrichment, ≥98% (+0.5%) $^{18}O$-isotope enrichment, or ≥99% (±0.5%)$^{18}O$-isotope enrichment. In a particular embodiment, the resultant Alpelisib-$^{18}O_1$ has ≥95% (±0.5%) $^{18}O$-isotope enrichment. In an embodiment, the molecular weight of Alpelisib-$^{18}O_1$ is 443.45. Preparation of Alpelisib-$^{18}O_1$ is further described in Example 1 below.

Compositions

In an embodiment, there is provided a pharmaceutical composition comprising an isotope-enriched compound described herein, e.g., a compound of Formulae I to III or of Table 1, or a pharmaceutically acceptable salt, ester, chelate, hydrate or solvate thereof, and a pharmaceutically acceptable carrier. In another embodiment, there is provided a pharmaceutical composition comprising a compound of Formula I to III or of Table 1, or a pharmaceutically acceptable salt thereof, and a pharmaceutically acceptable carrier. In another embodiment, there is provided a pharmaceutical composition comprising a compound of Formula I to III or of Table 1, or a pharmaceutically acceptable salt thereof, and a pharmaceutically acceptable carrier, with the proviso that the compound is not niraparib. In another embodiment, there is provided a pharmaceutical composition comprising isotope-enriched alpelisib, e.g., $^{18}O_1$-alpelisib, and a pharmaceutically acceptable carrier.

The preparation of pharmaceutical compositions can be carried out as known in the art (see, for example, Remington: The Science and Practice of Pharmacy, 20th Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

Any suitable pharmaceutically acceptable carriers, diluents, adjuvants, excipients, or vehicles may be used in compositions provided herein, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

A pharmaceutically acceptable carrier may include any and all solvents, dispersion media, coatings, antibacterial and antifungal agents, isotonic and absorption delaying agents, and the like that are physiologically compatible. In one embodiment, the carrier is suitable for oral administration. Alternatively, the carrier may be suitable for intravenous, intraperitoneal, intramuscular, sublingual or parenteral administration. In other embodiments, the carrier is suitable for topical administration or for administration via inhalation. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

In some embodiments, pharmaceutical compositions provided herein are suitable for oral administration. For example, a pharmaceutical composition may be in the form of a hard shell gelatin capsule, a soft shell gelatin capsule, a cachet, a pill, a tablet, a lozenge, a powder, a granule, a pellet, a pastille, or a dragee. In a particular embodiment, the pharmaceutical composition is in the form of a tablet.

Alternatively, a pharmaceutical composition may be in the form of a solution, an aqueous liquid suspension, a non-aqueous liquid suspension, an oil-in-water liquid emulsion, a water-in-oil liquid emulsion, an elixir, or a syrup.

Pharmaceutical compositions may or may not be enteric coated. In some embodiments, pharmaceutical compositions are formulated for controlled release, such as delayed or extended release.

In further embodiments, compounds and compositions thereof may be formulated in multi-dose forms, i.e., in the form of multi-particulate dosage forms (e.g., hard gelatin capsules or conventional tablets prepared using a rotary tablet press) comprising one or more bead or minitab populations for oral administration. The conventional tablets rapidly disperse on entry into the stomach. The one or more coated bead or minitab populations may be compressed together with appropriate excipients into tablets (for example, a binder, a diluent/filler, and a disintegrant for conventional tablets.

Tablets, pills, beads, or minitabs of the compounds and compositions of the compounds may be coated or otherwise compounded to provide a dosage form affording the advantage of controlled release, including delayed or extended release, or to protect from the acid conditions of the stomach. For example, the tablet or pill can include an inner dosage and an outer dosage component, the latter being in the form of a coating over the former. The two components can be separated by a polymer layer that controls the release of the inner dosage.

In certain embodiments, the layer may comprise at least one enteric polymer. In further embodiments, the layer may comprise at least one enteric polymer in combination with at least one water-insoluble polymer. In still further embodiments, the layer may comprise at least one enteric polymer in combination with at least one water-soluble polymer. In yet further embodiments, the layer may comprise at least one enteric polymer in combination with a pore-former.

In certain embodiments, the layer may comprise at least one water-insoluble polymer. In still further embodiments, the layer may comprise at least one water-insoluble polymer in combination with at least one water-soluble polymer. In yet further embodiments, the layer may comprise at least one water-insoluble polymer in combination with a pore-former.

Representative examples of water-soluble polymers include polyvinylpyrrolidone (PVP), hydroxypropyl methylcellulose (HPMC), hydroxypropylcellulose (HPC), polyethylene glycol, and the like.

Representative examples of enteric polymers include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit (LI 00, S I 00, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K. K.

Representative examples of useful water-insoluble polymers include ethylcellulose, polyvinyl acetate (for example, Kollicoat SR #30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Any of the above polymers may be further plasticized with one or more pharmaceutically acceptable plasticizers.

Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating an active compound, such as a compound of Formula I to III or of Table 1, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound for the prevention or treatment of a disease of interest, e.g., a PI3K mediated disease, such as a proliferative disease, such as melanoma, colorectal adenoma, breast cancer, or pancreatic cancer. Dosages are discussed further below.

In some embodiments, there are provided pharmaceutical compositions that comprise a therapeutically effective amount of a compound and/or composition described herein, and a pharmaceutically acceptable carrier. In an embodiment, there are provided pharmaceutical compositions for the treatment or prevention of a PI3K mediated disease, comprising a compound described herein, or a pharmaceutically acceptable salt thereof, and a pharmaceutically acceptable carrier. In another embodiment, there is provided a pharmaceutical composition for the prevention or treatment of a PI3K mediated disease, such as a proliferative disease, such as melanoma, colorectal adenoma, breast cancer, or pancreatic cancer, the composition comprising a compound described herein, or a pharmaceutically acceptable salt thereof, and a pharmaceutically acceptable carrier. In some such embodiments, the compound is $^{18}O_1$-alpelisib.

Supplementary active compounds can also be incorporated into the compositions provided herein. For example, a pharmaceutical composition provided herein may further comprise at least one additional therapeutic agent, as discussed below. In an embodiment, there are provided pharmaceutical compositions comprising at least one compound of the invention, together with a pharmaceutically acceptable carrier suitable for administration to a human or animal subject, either alone or together with one or more other therapeutic agent. In some embodiments, the additional therapeutic agent is an anticancer agent, e.g., fulvestrant. In one particular embodiment, the compound of the invention is $^{18}O_1$-alpelisib and the at least one additional therapeutic agent is fulvestrant.

Consequently, there is provided a combined pharmaceutical composition, e.g. for use in any of the methods described herein, comprising a compound of the invention in free form or pharmaceutically acceptable salt form in association with a pharmaceutically acceptable carrier. A combined pharmaceutical composition may comprise a compound of the invention in free form or in pharmaceutically acceptable salt form as active ingredient; one or more pharmaceutically acceptable carrier material(s); and optionally one or more further drug substances. Such combined pharmaceutical composition may be in the form of one dosage unit form or as a kit of parts. a combined pharmaceutical composition comprising a therapeutically effective amount of a compound of the invention in free form or in pharmaceutically acceptable salt form and a second drug substance, for simultaneous or sequential administration.

"Combination" refers to either a fixed combination in one dosage unit form, or a kit of parts for the combined administration where a compound of the invention and a combination partner (i.e., another therapeutic agent or drug as described further below), may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a combination partner, are both administered to a patient simultaneously in the form of a single entity or dosage. The term "non-fixed combination" means that the active ingredients, e.g. a compound of the invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

The amount of the compound of the invention in a formulation can vary within the full range employed by those skilled in the art. Typically, a formulation will contain, on a weight percent (wt %) basis, from about 0.01-99.99 wt % of a compound of the invention based on the total formulation, with the balance being one or more suitable pharmaceutical excipients. In some embodiments, the compound is present at a level of about 1-80 wt %. Dosages are discussed further below.

The present invention also provides a kit including one or more compound of the invention and optionally a combination partner as disclosed herein. In one embodiment, a kit comprises a compound or composition of the invention and a package insert or other labeling including directions for use thereof. Kits may optionally include one or more additional component such as acids, bases, buffering agents, inorganic salts, solvents, antioxidants, preservatives, or metal chelators; devices for delivery and administration such as syringes, vials, and the like; and instructions for use thereof.

Methods of Use

The invention provides methods of treating or preventing disease comprising administration of the compounds and compositions of the invention to a subject in need thereof. Without wishing to be limited by theory, it is believed that isotope-enriched compounds provided herein can improve therapeutic efficacy of a compound by improving its therapeutic bio-distribution and/or pharmacokinetic profiles, for example by increasing bioavailability of the compound, reducing metabolism of the compound, increasing compound stability, and/or changing the release rate of an active compound from a prodrug.

In an embodiment, the invention relates to methods of modulating the metabolism or the pharmacokinetic profile of an amide-bond containing (i.e., an amide functional group containing) compound in a subject, comprising administering to the subject an isotope-enriched compound and/or a pharmaceutical composition as described herein, wherein the metabolism or the pharmacokinetic profile of the amide-bond containing compound is modulated compared to administration of the same compound having only isotopes of natural abundance (i.e., the non-isotope-enriched compound). In some embodiments, there is provided a method of reducing the metabolism of a compound, reducing a compound's therapeutic toxicity, reducing a compound's adverse effects, increasing tolerability of a compound, improving biodistribution of a compound, and/or increasing the therapeutic or prophylactic effect of a compound in a subject, the method comprising administering to the subject an isotope-enriched compound or pharmaceutical composition as described herein, wherein the isotope-enriched compound's metabolism is reduced, therapeutic toxicity is reduced, adverse effects are reduced, tolerability is increased, biodistribution is improved, and/or therapeutic or prophylactic effect is increased as compared to administration of the compound having only isotopes of natural abundance (i.e., the non-isotope-enriched compound).

In one exemplary embodiment, the invention relates to a method of modulating, e.g., reducing, the metabolism of alpelisib comprising administering to the subject an isotope-enriched alpelisib compound and/or a pharmaceutical composition thereof as described herein, wherein the metabolism of the isotope-enriched alpelisib compound is modulated compared to administration of the same compound having only isotopes of natural abundance (i.e., the non-isotope-enriched compound). In some such embodiments, the isotope-enriched alpelisib is $^{18}O_1$-alpelisib. In an embodiment, the $^{18}O_1$-alpelisib is about 93% $^{18}O_1$-enriched, about 94% $^{18}O_1$-enriched, about 95% $^{18}O_1$-enriched, about 96% $^{18}O_1$-enriched, about 97% $^{18}O_1$-enriched, about 98% $^{18}O_1$-enriched, or about 99% $^{18}O_1$-enriched. In an embodiment, the $^{18}O_1$-alpelisib is administered in combination with at least one additional therapeutic agent, e.g., an anti-cancer drug, e.g., fulvestrant.

In an embodiment, the invention relates to the treatment of a PI3K mediated disease, i.e., a disease or condition ameliorated by inhibition of phosphoinositide 3-kinase (PI3K). In some embodiments, a phosphoinositide 3-kinase (PI3K) mediated disease is a PI3K alpha mediated disease (or disease mediated by overexpression or amplification of PI3K alpha, somatic mutation of PI3K or germline mutations or somatic mutation of PTEN or mutations and translocation of p85alpha that serve to upregulate the p85-p110 complex), especially such disorders that respond in a beneficial way to the inhibition of a PI3 kinase, especially inhibition of PI3K alpha or a mutant form thereof.

In some embodiments, a PI3K mediated disease is a cellular proliferative disease such as a tumor or cancerous cell growth. PI3K mediated diseases may include those showing overexpression or amplification of PI3K alpha, somatic mutation of PIK3CA or germline mutations or somatic mutation of PTEN or mutations and translocation of p85α that serve to up-regulate the p85-p110 complex. In particular embodiments, the compounds of the invention are useful in the treatment of human or animal (e.g., murine) cancers, including, for example, sarcoma; lung; bronchus; prostate; breast (including sporadic breast cancers and sufferers of Cowden disease); pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; a leukemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; a mammary carcinoma; basal cell carcinoma; squamous cell carcinoma; actinic keratosis; tumor diseases, including solid tumors; a tumor of the neck or head; polycythemia vera; essential thrombocythemia; myelofibrosis with myeloid metaplasia; and/or Walden stroem disease.

In other embodiments, a PI3K mediated disease is selected from the group consisting of: polycythemia vera, essential thrombocythemia, myelofibrosis with myeloid metaplasia, asthma, COPD, ARDS, Loffler's syndrome, eosinophilic pneumonia, parasitic (in particular metazoan)

infestation (including tropical eosinophilia), bronchopulmonary aspergillosis, polyarteritis nodosa (including Churg-Strauss syndrome), eosinophilic granuloma, eosinophil-related disorders affecting the airways occasioned by drug-reaction, psoriasis, contact dermatitis, atopic dermatitis, alopecia greata, erythema multiforme, dermatitis herpetiformis, scleroderma, vitiligo, hypersensitivity angiitis, urticaria, bullous pemphigoid, lupus erythematosus, pemphisus, epidermolysis bullosa acquisita, autoimmune haematogical disorders (e.g. haemolytic anaemia, aplastic anaemia, pure red cell anaemia and idiopathic thrombocytopenia), systemic lupus erythematosus, polychondritis, scleroderma, Wegener granulomatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), interstitial lung fibrosis, psoriatic arthritis, glomerulonephritis, cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease, reperfusion injuries, retinopathy, such as diabetic retinopathy or hyperbaric oxygen-induced retinopathy, and conditions characterized by elevated intraocular pressure or secretion of ocular aqueous humor, such as glaucoma.

In some embodiments, the PI3K mediated disease is a proliferative disease, e.g., melanoma, colorectal adenoma, breast cancer, and/or pancreatic cancer. In some such embodiments, the breast cancer is hormone receptor positive (HR+) and human epidermal growth factor receptor negative (HER2-). In some embodiments, the breast cancer is PIK3CA mutated.

For the above uses the required dosage will of course vary depending on the mode of administration, the particular condition to be treated and the effect desired. In general, satisfactory results are indicated to be obtained systemically at daily dosages of from about 0.03 to about 100.0 mg/kg per body weight, e.g. about 0.03 to about 10.0 mg/kg per body weight. An indicated daily dosage in humans is generally in the range from about 0.5 mg to about 3 g, e.g. about 5 mg to about 1.5 g, conveniently administered, for example, in divided doses up to four times a day or in retard form or once a day. Suitable unit dosage forms for oral administration comprise from ca. 0.1 to about 500 mg, e.g. about 1.0 to about 500 mg active ingredient, e.g., 50 mg active ingredient, 100 mg active ingredient, 150 mg active ingredient, 200 mg active ingredient, 250 mg active ingredient, 300 mg active ingredient, or 500 mg active ingredient. In one embodiment, the compound of the invention is administered at a daily dosage of about 300 mg. In some such embodiments, the compound is administered once daily. In some such embodiments, the compound is administered once daily orally with food.

The compounds of the invention may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, by inhalation, intranasally, or in a suppository form. In a particular embodiment, the compound is administered orally, in tablet form.

The compounds of the invention may be administered in free form or in pharmaceutically acceptable salt form. Such salts may be prepared in a conventional manner and generally exhibit the same order of activity as the free compounds, as discussed hereinabove.

The PI3K pathway is a central oncogenic pathway that regulates cell proliferation, cell metabolism, growth, survival, and apoptosis, with activation of PI3K downstream signaling critical in mediating the transforming potential of oncogenes and tumor suppressors in many tumor types. Dysregulation of PI3K signaling is associated with the development of resistance to numerous forms of treatment, including antiestrogens, trastuzumab, radiotherapy, and chemotherapy. PIK3CA mutations are reported in up to 43.3% of HR-positive, HER2-negative tumors (Wan et al., 2018). These mutations increase PI3K activity and induce mammary tumor formation in transgenic mice (Zhao and Vogt, 2008; Meyer et al., 2011; Miller et al., 2011).

Consequently, there is also provided a method for preventing or treating conditions, disorders or diseases mediated by the activation of PI3K enzyme, e.g. in a subject in need of such treatment, which method comprises administering to said subject an effective amount of a compound of the invention (e.g., $^{18}O_1$-alpelisib) or a pharmaceutically acceptable salt thereof, in free form or in a pharmaceutically acceptable salt form as a pharmaceutical, e.g., in any of the methods as indicated herein. $^{18}O_1$-alpelisib inhibit PI3K, predominantly by inhibiting PI3Kα; gain-of-function mutations in PIK3CA lead to activation of PI3Kα and Protein Kinase B (Akt)-signaling, cellular transformation and the generation of tumors in in vitro and in vivo models.

Evidence is also emerging that the combination of a PI3K inhibitor with inhibitors of other pathways will be useful in treating cancer and proliferative diseases in humans. Consequently, there is also provided a method for preventing or treating conditions, disorders or diseases mediated by the activation of PI3K enzyme, e.g. in a subject in need of such treatment, which method comprises administering to said subject an effective amount of a compound of the invention (e.g., $^{18}O_1$-alpelisib) or a pharmaceutically acceptable salt thereof, in free form or in a pharmaceutically acceptable salt form as a pharmaceutical, e.g., in any of the methods as indicated herein, and further comprising administration of at least one additional anti-cancer agent as described herein.

Although breast cancer affects a single anatomic site, it is a heterogeneous disease that has phenotypically various presentations (Perou et al., 2000; Serlie et al., 2001). Identification of different biological subtypes occurs primarily through the use of immunohistochemistry (Nielsen et al., 2004) and gene expression profiling (Perou et al., 2000), with breast cancer broken down into three biologic subgroups: those that express estrogen receptors (ERs), those that express HER2 (with or without ER expression), and those that do not express either of these, nor the progesterone receptor (PR; triple-negative) (Fragomeni et al., 2018). Approximately 70% of invasive breast cancers in women >45 years of age express ER and/or PR, but not HER2, and are termed HR-positive, HER2-negative (Huang et al., 2005). While the most common subtype of breast cancer in men is HR-positive, HER2-negative (Anderson et al., 2004; Ottini et al., 2010), much less is known about the biology of male breast cancer due to the low prevalence of the condition in men and the historical exclusion of men from breast cancer clinical trials.

Patients with ER-positive metastatic breast cancer often respond to endocrine therapy alone or in combination with targeted agents, which can reduce tumor burden and symptoms with generally fewer side effects and toxicities than chemotherapy (Ma and Sparano, 2020). Adrenal precursors, testosterone, and androstenedione are converted to estradiol and estrone by aromatase activity, with specific inhibitors of aromatase (anastrozole, letrozole, and exemestane) demonstrating efficacy in depleting estrogen; additionally, tamoxifen is available as an effective therapy option that acts by interfere with ER signaling (Ma and Sparano, 2020).

Modern endocrine therapies prolong disease progression, but do not provide a cure, with the principle goal of therapy being palliative care (Ma and Sparano, 2020). However, endocrine resistance is a major problem, with a distinction made between primary (de novo) and secondary (developed during the course of treatment) resistance; only 50% of patients with ER-positive breast cancer benefit from first-line endocrine therapy, and all of those who respond initially will acquire resistance, with tumor relapse and growth (Fu et al., 2013). Even in patients who develop secondary endocrine resistance, progression-free survival is short with endocrine-based treatment options. When a patient's cancer fails to respond or stops responding to a given line of endocrine therapy or a targeted agent, an important consideration in whether or not to proceed with another line of endocrine therapy or to move to chemotherapy is PIK3CA mutation status (Ma and Sparano, 2020).

Approximately 20-30% of human breast cancers overexpress Her-2/neu-ErbB2, the target for the drug trastuzumab. Although trastuzumab has demonstrated durable responses in some patients expressing Her2/neu-ErbB2, only a subset of these patients respond. Recent work has indicated that this limited response rate can be substantially improved by the combination of trastuzumab with inhibitors of PI3K or the PI13K/AKT pathway (Chan et al., Breast Can. Res. Treat. 91:187 (2005), Woods Ignatoski et al., Brit. J. Cancer 82:666 (2000), Nagata et al., Cancer Cell 6:117 (2004)).

A variety of human malignancies express activating mutations or increased levels of Her1/EGFR and a number of antibody and small molecule inhibitors have been developed against this receptor tyrosine kinase including tarceva, gefitinib and erbitux. However, while EGFR inhibitors demonstrate anti-tumor activity in certain human tumors (e.g., NSCLC), they fail to increase overall patient survival in all patients with EGFR-expressing tumors. This may be rationalized by the fact that many downstream targets of Her1/EGFR are mutated or deregulated at high frequencies in a variety of malignancies, including the PI3K/Akt pathway. For example, gefitinib inhibits the growth of an adenocarcinoma cell line in in vitro assays. Nonetheless, sub-clones of these cell lines can be selected that are resistant to gefitinib that demonstrate increased activation of the PI3/Akt pathway. Down-regulation or inhibition of this pathway renders the resistant sub-clones sensitive to gefitinib (Kokubo et al., Brit. J. Cancer 92:1711 (2005)). Furthermore, in an in vitro model of breast cancer with a cell line that harbors a PTEN mutation and over-expresses EGFR inhibition of both the PI3K/Akt pathway and EGFR produced a synergistic effect (She et al., Cancer Cell 8:287-297 (2005)). These results indicate that the combination of gefitinib and PI3K/Akt pathway inhibitors would be an attractive therapeutic strategy in cancer.

The combination of AEE778 (an inhibitor of Her-2/neu/ErbB2, VEGFR and EGFR) and RAD001 (an inhibitor of mTOR, a downstream target of Akt) produced greater combined efficacy that either agent alone in a glioblastoma xenograft model (Goudar et al., Mol. Cancer. Ther. 4:101-112 (2005)).

Anti-estrogens, such as tamoxifen, inhibit breast cancer growth through induction of cell cycle arrest that requires the action of the cell cycle inhibitor p27Kip. It has been shown that activation of the Ras-Raf-MAP Kinase pathway alters the phosphorylation status of p27Kip such that its inhibitory activity in arresting the cell cycle is attenuated, thereby contributing to anti-estrogen resistance (Donovan, et al, J. Biol. Chem. 276:40888, (2001)). As reported by Donovan et al., inhibition of MAPK signaling through treatment with MEK inhibitor reversed the aberrant phosphorylation status of p27 in hormone refractory breast cancer cell lines and in so doing restored hormone sensitivity. Similarly, phosphorylation of p27Kip by Aid also abrogates its role to arrest the cell cycle (Viglietto et al., Nat. Med. 8:1145 (2002)).

Accordingly, in a further embodiment, the compounds of the invention (e.g., $^{18}O_1$-alpelisib) are used in the treatment of hormone dependent cancers, such as breast and prostate cancers. By this use, it is aimed to reverse hormone resistance commonly seen in these cancers with conventional anticancer agents.

In hematological cancers, such as chronic myelogenous leukemia (CML), chromosomal translocation is responsible for the constitutively activated BCR-Abl tyrosine kinase. The afflicted patients are responsive to imatinib, a small molecule tyrosine kinase inhibitor, as a result of inhibition of Abl kinase activity. However, many patients with advanced stage disease respond to imatinib initially, but then relapse later due to resistance-conferring mutations in the Abl kinase domain. In vitro studies have demonstrated that BCR-Abl employs the Ras-Raf kinase pathway to elicit its effects. In addition, inhibiting more than one kinase in the same pathway provides additional protection against resistance-conferring mutations.

Accordingly, in another embodiment, the compounds of the invention (e.g., $^{18}O_1$-alpelisib) are used in combination with at least one additional agent selected from the group of kinase inhibitors, such as Gleevec™, in the treatment of hematological cancers, such as chronic myelogenous leukemia (CML). By this use, it is aimed to reverse or prevent resistance to said at least one additional agent.

Because activation of the PI3K/Akt pathway drives cell survival, inhibition of the pathway in combination with therapies that drive apoptosis in cancer cells, including radiotherapy and chemotherapy, will result in improved responses (Ghobrial et al., CA Cancer J. Clin 55:178-194 (2005)). As an example, combination of PI3 kinase inhibitor with carboplatin demonstrated synergistic effects in both in vitro proliferation and apoptosis assays as well as in in vivo tumor efficacy in a xenograft model of ovarian cancer (Westfall and Skinner, Mol. Cancer Ther. 4:1764-1771 (2005)).

In addition to cancer and proliferative diseases, there is accumulating evidence that inhibitors of Class 1A and 1B PI3 kinases would be therapeutically useful in others disease areas. The inhibition of p110β, the PI3K isoform product of the PIK3CB gene, has been shown to be involved in shear-induced platelet activation (Jackson et al., Nature Medicine 11:507-514 (2005)). Thus, a PI3K inhibitor that inhibits p110β would be useful as a single agent or in combination in anti-thrombotic therapy. The isoform p110δ, the product of the PIK3CD gene, is important in B cell function and differentiation (Clayton et al., J. Exp. Med. 196:753-763 (2002)), T-cell dependent and independent antigen responses (Jou et al., Mol. Cell. Biol. 22:8580-8590 (2002)) and mast cell differentiation (Ali et al., Nature 431:1007-1011 (2004)). Thus, it is expected that p110δ-inhibitors would be useful in the treatment of B-cell driven autoimmune diseases and asthma. Finally, the inhibition of p110γ, the isoform product of the PI3KCG gene, results in reduced T, but not B cell, response (Reif et al., J. Immunol. 173:2236-2240 (2004)) and its inhibition demonstrates efficacy in animal models of autoimmune diseases (Camps et al., Nature Medicine 11:936-943 (2005), Barber et al., Nature Medicine 11:933-935 (2005)).

In another embodiment, there is provided a method of treating human or animal subjects suffering from a cellular proliferative disease, such as cancer. There are provided methods of treating a human or animal subject in need of such treatment, comprising administering to the subject a therapeutically effective amount of a compound of the invention (e.g., $^{18}O_1$-alpelisib), either alone or in combination with one or more other anticancer agents. In particular, compositions will either be formulated together as a combination therapeutic or administered separately. Suitable anticancer agents for use with a compound of the invention include, but are not limited to, one or more compounds selected from the group consisting of: kinase inhibitors, anti-estrogens, anti-androgens, other inhibitors, cancer chemotherapeutic drugs, alkylating agents, chelating agents, biological response modifiers, cancer vaccines, and agents for antisense therapy, as set forth further below.

Kinase inhibitors for use as anticancer agents in conjunction with the compounds of the invention include, without limitation, inhibitors of Epidermal Growth Factor Receptor (EGFR) kinases such as small molecule quinazolines, for example gefitinib (U.S. Pat. Nos. 5,457,105, 5,616,582, and 5,770,599), ZD-6474 (WO 01/32651), erlotinib (Tarceva™, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. Nos. 6,605,617 and 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin™ (WO 94/10202), KRN-951, 3-[5-(methylsulfonylpiperadine methyl)-indolyl]-quinolone, AG-13736 and AG-13925, pyrrolo[2,1-t][1,2,4]triazines, ZK-304709, Veglin™, VMDA-3601, EG-004, CEP-701 (U.S. Pat. No. 5,621,100), Candy (WO 04/09769); Erb2 tyrosine kinase inhibitors such as pertuzumab (WO 01/00245), trastuzumab, and rituximab; Aid protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PDGFR) kinase inhibitors such as CHIR-258, 3G3 mAb, AG-13736, SU-11248 and SU6668; and Bcr-Abl kinase inhibitors and fusion proteins such as STI-571 or Gleevec™ (imatinib).

Estrogen-targeting agents (anti-estrogens) for use in anticancer therapy in conjunction with the compounds of the invention include, without limitation, Selective Estrogen Receptor Modulators (SERMs) including tamoxifen, toremifene, raloxifene; aromatase inhibitors including anastrozole (Arimidex™); and Estrogen Receptor Downregulators (ERDs) including fulvestrant (Faslodex™).

Fulvestrant is a small molecule drug used for treatment of hormone receptor (HR)-positive metastatic breast cancer in post-menopausal women with disease progression following anti-estrogen therapy. It is an estrogen receptor antagonist with no agonist effects, which works both by down-regulating and by degrading the estrogen receptor. Currently it is used both as monotherapy for the treatment of breast cancers and in combination with alpelisib for the treatment of HR-positive, human epidermal growth factor receptor 2 (HER2)-negative, PIK3CA-mutated, advanced or metastatic breast cancer. In one particular embodiment, fulvestrant is used in conjunction with the compounds of the invention, e.g. $^{18}O$-alpelisib, for the treatment of breast cancer, e.g. hormone receptor (HR)-positive, human epidermal growth factor receptor 2 (HER2)-negative, PIK3CA-mutated, advanced or metastatic breast cancer.

Androgen-targeting agents (anti-androgens) for use in anticancer therapy in conjunction with the compounds of the invention include, without limitation, flutamide, bicalutamide, finasteride, aminoglutethamide, ketoconazole, and corticosteroids.

Other inhibitors for use as anticancer agents in conjunction with the compounds of the invention include, without limitation, protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; proteasome modulators such as bortezomib or Velcade™ (U.S. Pat. No. 5,780,454), XL-784; and cyclooxygenase 2 (COX-2) inhibitors including non-steroidal antiinflammatory drugs I (NSAIDs).

Cancer chemotherapeutic agents for use as anticancer agents in conjunction with the compounds of the invention include, without limitation, anastrozole (Arimidex™), bicalutamide (Casodex™), bleomycin sulfate (Blenoxane™), busulfan (Myleran™), busulfan injection (Busulfex™), capecitabine (Xeloda™), N4-pentoxycarbonyl-5-deoxy-5-fluorocytidine, carboplatin (Paraplatin™), carmustine (BiCNU™), chlorambucil (Leukeran™), cisplatin (Platinol™), cladribine (Leustatin™), cyclophosphamide (Cytoxan™ or Neosar™), cytarabine, cytosine arabinoside (Cytosar-U™), cytarabine liposome injection (DepoCyt™), dacarbazine (DTIC-Dome™), dactinomycin (Actinomycin D, Cosmegan), daunorubicin hydrochloride (Cerubidine™), daunorubicin citrate liposome injection (DaunoXome™), dexamethasone, docetaxel (Taxotere™), doxorubicin hydrochloride (Adriamycin™, Rubex™), etoposide (Vepesid™), fludarabine phosphate (Fludara™), 5-fluorouracil (Adrucil™, Efudex™), flutamide (Eulexin™), tezacitibine, Gemcitabine (difluorodeoxycitidine), hydroxyurea (Hydrea™), Idarubicin (Idamycin™), ifosfamide (IFEX™), irinotecan (Camptosar™), L-asparaginase (ELSPAR™), leucovorin calcium, melphalan (Alkeran™), 6-mercaptopurine (Purinethol™), methotrexate (Folex™), mitoxantrone (Novantrone™), mylotarg, paclitaxel (Taxol™), phoenix (Yttrium90/MX-DTPA), pentostatin, polifeprosan 20 with carmustine implant (Gliadel™), tamoxifen citrate (Nolvadex™), teniposide (Vumon™), 6-thioguanine, thiotepa, tirapazamine (Tirazone™), topotecan hydrochloride for injection (Hycamptin™), vinblastine (Velban™), vincristine (Oncovin™), and vinorelbine (Navelbine™).

Alkylating agents for use in conjunction with the compounds of the invention include, without limitation, VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); O6-benzylguanine; decitabine (5-aza-2-deoxycytidine); brostallicin; mitomycin C (MitoExtra); TLK-286 (Telcyta™); temozolomide; trabectedin (U.S. Pat. No. 5,478,932); AP-5280 (Platinate formulation of Cisplatin); porfiromycin; and clearazide (meclorethamine).

Chelating agents for use in conjunction with the compounds of the invention include, without limitation, tetrathiomolybdate (WO 01/60814); RP-697; Chimeric T84.66 (cT84.66); gadofosveset (Vasovist™); deferoxamine; and bleomycin optionally in combination with electorporation (EPT).

Biological response modifiers, such as immune modulators, for use in conjunction with the compounds of the invention include, without limitation, staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-α, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexylen™); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

Anticancer vaccines for use in conjunction with the compounds of the invention include, without limitation, Avicine™ (Tetrahedron Lett. 26:2269-70 (1974)); oregovomab (OvaRex™); Theratope™ (STn-KLH); Melanoma Vaccines; GI-4000 series (GI-4014, GI-4015, and GI-4016), which are directed to five mutations in the Ras protein; GlioVax-1; MelaVax; Advexin™ or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

Anticancer agents for use in conjunction with the compounds of the invention also include antisense compositions, such as, without limitation, AEG-35156 (GEM-640); AP-12009 and AP-11014 (TGF-beta2-specific antisense oligonucleotides); AVI-4126; AVI-4557; AVI-4472; oblimersen (Genasense™); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sima-027 (RNAi-based therapeutic targeting VEGFR-1 mRNA).

The compounds of the invention can also be combined in a pharmaceutical composition with bronchodilatory or antihistamine drugs substances. Such bronchodilatory drugs include without limitation anticholinergic or antimuscarinic agents, in particular ipratropium bromide, oxitropium bromide, and tiotropium bromide, and .beta.-2-adrenoreceptor agonists such as salbutamol, terbutaline, salmeterol, carmoterol, milveterol and, especially, formoterol or indacaterol. Co-therapeutic antihistamine drug substances include cetirizine hydrochloride, clemastine fumarate, promethazine, loratadine, desloratadine diphenhydramine and fexofenadine hydrochloride.

The compounds of the invention can also be used in combination with one or more compound useful for the treatment of a thrombolytic disease, heart disease, stroke, and the like. Such compounds include without limitation aspirin, a streptokinase, a tissue plasminogen activator, a urokinase, a anticoagulant, antiplatelet drugs (e.g, PLAVIX™; clopidogrel bisulfate), a statin (e.g., LIPITOR™ or Atorvastatin calcium), ZOCOR™ (Simvastatin), CRESTOR™ (Rosuvastatin), etc.), a Beta blocker (e.g., Atenolol), NORVASC™ (amlodipine besylate), and an ACE inhibitor (e.g., lisinopril).

The compounds of the invention can also be used in combination with one or more compounds that are useful for the treatment of antihypertension. Such compounds include without limitation ACE inhibitors, lipid lowering agents such as statins, LIPITOR™ (Atorvastatin calcium), and calcium channel blockers such as NORVASC™ (amlodipine besylate).

The compounds of the invention can also be used in combination with one or more compounds selected from the group consisting of fibrates, beta-blockers, NEPI inhibitors, Angiotensin-2 receptor antagonists and platelet aggregation inhibitors.

The compounds of the invention can also be used in combination with one or more compounds suitable for the treatment of inflammatory diseases, including rheumatoid arthritis. Such compound may be selected from the group consisting of TNFα inhibitors such as anti-TNF-α monoclonal antibodies (such as REMICADE™, CDP-870) and D2E7 (HUMIRA™) and TNF receptor immunoglobulin fusion molecules (such as ENBREL™), IL-1 inhibitors, receptor antagonists or soluble IL-1Rα (e.g. KINERET or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX (celecoxib), PREXIGE (lumiracoxib)), metalloprotease inhibitors (preferably MMP-13 selective inhibitors), p2x7 inhibitors, α2αinhibitors, NEUROTIN, pregabalin, low dose methotrexate, leflunomide, hydroxychloroquine, d-penicillamine, auranofin or parenteral or oral gold.

The compounds of the invention can also be used in combination with one or more compounds suitable for the treatment of osteoarthritis. Such compound may be selected from the group consisting of, without limitation, standard non-steroidal anti-inflammatory agents (hereinafter NSAID's) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, lumiracoxib and etoricoxib, analgesics and intraarticular therapies such as corticosteroids and hyaluronic acids such as hyalgan and synvisc.

The compounds of the invention can also be used in combination with an antiviral agent and/or an antisepsis compound. Such antiviral agent may be selected for example from the group consisting of Viracept, AZT, acyclovir and famciclovir. Such antisepsis compound may be selected for example from the group consisting of Valant.

The compounds of the invention can also be used in combination with one or more agents selected from the group consisting of CNS agents such as antidepressants (sertraline), anti-Parkinsonian drugs (such as deprenyl, L-dopa, Requip, Mirapex; MAOB inhibitors (such as selegine and rasagiline); comP inhibitors (such as Tasmar); A-2 inhibitors; dopamine reuptake inhibitors; NMDA antagonists; Nicotine agonists; Dopamine agonists; and inhibitors of neuronal nitric oxide synthase). The compounds of the invention can also be used in combination with one or more anti-Alzheimer's drugs. Such anti-Alzheimer Drug may be selected from the group consisting of donepezil, tacrine, α2δinhibitors, NEURONTIN™, pregabalin, COX-2 inhibitors, propentofylline or metrifonate.

The compounds of the invention can also be used in combination with anosteoporosis agents and/or an immunosuppressant agent. Such osteoporosis agents may be selected from the group consisting of EVISTA™ (raloxifene hydrochloride), droloxifene, lasofoxifene or fosomax. Such immunosuppressant agents may be selected from the group consisting of FK-506 and rapamycin.

In general, the compounds of the invention will be administered in a therapeutically effective amount by any of the accepted modes of administration for agents that serve similar utilities. The actual amount of the compound of the invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day. All of these factors are within the skill of the attending clinician. Therapeutically effective amounts of compounds of the invention may range from about 0.05 to about 50 mg per kilogram body weight of the recipient per day; preferably about 0.1-25 mg/kg/day, more preferably from about 0.5 to 10 mg/kg/day. Thus, for administration to a 70 kg person, the dosage range would most preferably be about 35-70 mg per day. In one embodiment, the therapeutically effective amount is 300 mg/day, optionally administered once daily.

In general, compounds of the invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the formula (I) is inhalation. This is an effective method for delivering a therapeutic agent directly to the respiratory tract.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free-flowing powder that can be dispersed in the patient's inspiratory air-stream during breathing by the device. In order to achieve a free-flowing powder, the therapeutic agent is formulated with an excipient such as lactose. A measured amount of the therapeutic agent is stored in a capsule form and is dispensed with each actuation. In some embodiments the invention also relates to formulations wherein the particle size of a compound of the invention is between 10-1000 nm, preferably 10-400 nm. Such pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

It should be understood that the dosage or amount of a compound and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens may depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a compound or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined as known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in compositions provided herein. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg, about 250 mg, or about 500 mg and, for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound of the invention which is effective at such dosage or as a multiple of the same, for instance, units containing 5 mg to 500 mg, usually around 10 mg to 200 mg, 50 mg, 100 mg, 150 mg, 200 mg, 250 mg, 300 mg, 350 mg, or 400 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, or 500 mg) of a compound described herein.

In some embodiments, the dosage range for oral administration is generally about 0.001 mg to about 2000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

In further embodiments, the dose is about 10 mg to about 1000 mg, including all ranges and subranges there between, e.g., about 10 mg to about 900 mg, about 10 mg to about 800 mg, about 10 to about 700 mg, about 10 mg to about 600 mg, about 10 mg to about 500 mg, about 10 mg to about 400 mg, about 10 mg to about 300 mg, about 10 mg to about 250 mg, about 10 mg to about 200 mg, about 10 mg to about 150 mg, about 10 mg to about 100 mg, about 10 mg to about 50 mg, about 50 mg to about 900 mg, about 50 mg to about 800 mg, about 50 to about 700 mg, about 50 mg to about 600 mg, about 50 mg to about 500 mg, about 50 mg to about 400 mg, about 50 mg to about 300 mg, about 50 mg to about 250 mg, about 50 mg to about 200 mg, about 50 mg to about 150 mg, about 50 mg to about 100 mg, about 100 mg to about 900 mg, about 100 mg to about 800 mg, about 100 to about 700 mg, about 100 mg to about 600 mg, about 100 mg to about 500 mg, about 100 mg to about 400 mg, about 100 mg to about 300 mg, about 100 mg to about 250 mg, about 100 mg to about 200 mg, about 100 mg to about 150 mg, about 150 mg to about 200 mg, about 150 mg to about 250 mg, about 150 to about 300 mg, about 150 mg to about 400 mg, about 150 mg to about 500 mg, about 200 mg to about 900 mg, about 200 mg to about 800 mg, about 200 to about 700 mg, about 200 mg to about 500 mg, about 200 mg to about 400 mg, about 200 mg to about 300 mg, about 200 mg to about 250 mg, about 300 mg to about 900 mg, about 300 mg to about 800 mg, about 300 to about 700 mg, about 300 to about 600 mg, about 300 mg to about 500 mg, about 300 mg to about 400 mg, about 400 mg to about 900 mg, about 400 mg to about 800 mg, about 400 mg to about 700 mg, about 400 mg to about 600 mg, about 400 mg to about 500 mg, about 500 mg to about 900 mg, about 500 mg to about 800 mg, about 500 to about 700 mg, about 500 to about 600 mg, about 100 mg to about 500 mg, about 100 mg to about 400 mg, about 100 mg to about 300 mg, or about 100 mg to about 250 mg. In an embodiment, the range is about 150 mg to about 400 mg.

In still further embodiments, the dose is 10 mg, 25 mg, 50 mg, 60 mg, 70 mg, 75 mg, 80 mg, 85 mg, 90 mg, 100 mg, 105 mg, 1 10 mg, 1 15 mg, 120 mg, 125 mg, 130 mg, 135 mg, 140 mg, 145 mg, 150 mg, $^{16}$O mg, 170 mg, 180 mg, 190 mg, 200 mg, 225 mg, 250 mg, 275 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg.

In an embodiment, the dose is 300 mg daily, e.g., 300 mg administered once daily, optionally with food.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1: Preparation of N-(4-methyl-5-(2-(2,2,2-trifluoro-1,1-dimethylethyl)-4 pyridinyl)-2-thiazolyl) aminocarbonyl-L-prolin-$^{18}$O-amide (Compound 1, or Alpelisib-$^{18}$O$_1$)

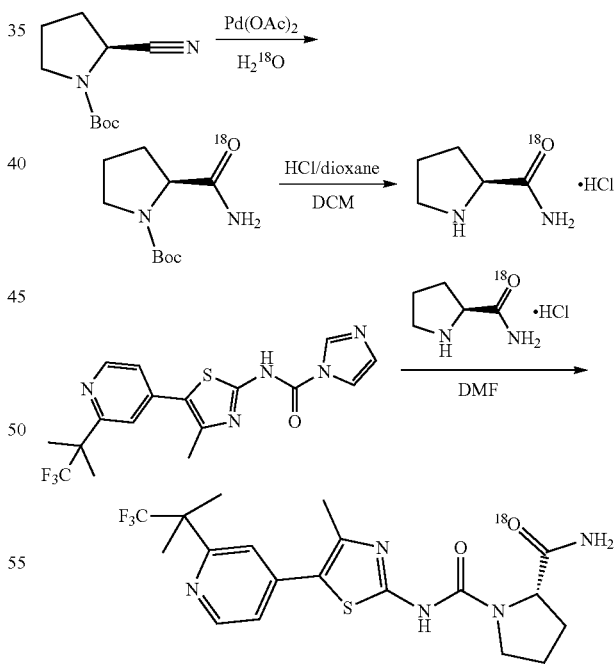

1-(tert-Butoxycarbonyl)-2-cyanopyrrolidine (100 mg, 0.51 mmol), palladium acetate (12 mg, 0.051 mmol), and 2,2'-bipyridine (8 mg, 0.051 mmol) were mixed with $^{18}$O-water (98% $^{18}$O-enrichment, 0.5 mL; also referred to as H$_2$$^{18}$O) in a sealed tube. The mixture was stirred at 60° C. under nitrogen atmosphere in the sealed tube for 24 hours. The reaction mixture was cooled to room temperature and concentrated in vacuum. The residual material was purified by flash column chromatography (gradient eluent, DCM:MeOH from 100:0 to 50:1), affording N-Boc-L-prolin-$^{18}$O-amide (48 mg; $^{18}$O-enrichment, 97.3%). To a solution of N-Boc-L-prolin-$^{18}$O-amide (48 mg, 0.22 mmol) in DCM (0.5 mL) was added 4M HCl/dioxane (0.5 mL). The mixture was stirred at 25° C. for 1 h. The reaction mixture was concentrated in vacuum to afford L-prolin-$^{18}$O-amide hydrochloride (35 mg). L-prolin-$^{18}$O-amide hydrochloride (33 mg, 0.22 mmol) was added to a solution of N-(4-methyl-5-(2-(2,2,2-trifluoro-2-methylpropan-2-yl)pyridin-4-yl)thiazol-2-yl)-1H-imidazole-1-carboxamide (79 mg, 0.2 mmol) in DMF (1 mL), followed by addition of triethylamine (80 mg, 0.8 mmol). The reaction mixture was stirred at 30° C. for 16 h. DMF was removed under reduced pressure. The residual material was purified by flash column chromatography (eluent, DCM:MeOH, from 100:0 to 30:1) to give the title compound (1, 70 mg, 81.9% yield; $^{18}$O-enrichment, 97.3%): $^1$H NMR (500 MHz, DMSO-d$_6$) δ ppm 10.96 (s, 1H), 8.60 (d, J=5.0 Hz, 1H), 7.55 (s, 1H), 7.41 (s, 2H), 6.97 (s, 1H), 4.26 (s, 0.48H), 3.60 (s, 1H), 3.46 (s, 1H), 2.42 (s, 4H), 2.09 (s, 1H), 1.87 (s, 3H), 1.61 (s, 6H); $^{13}$C NMR (125 MHz, DMSO-d6) δ ppm 174.36, 159.87, 158.99, 152.99, 149.58, 145.69, 141.44, 129.94, 127.69, 121.80, 120.78, 60.36, 55.40, 46.92, 46.71, 30.43, 21.93, 16.89. m/z (ESI$^+$) 443.7, m/z (ESI$^-$) 441.5.

Example 2: Preparation of N-(4-methyl-5-(2-(2,2,2-trifluoro-1,1-dimethylethyl)-4 pyridinyl)-2-thiazolyl) aminocarbonyl-L-prolin-$^{17}$O-amide (Compound 2, or Alpelisib-$^{17}$O$_1$)

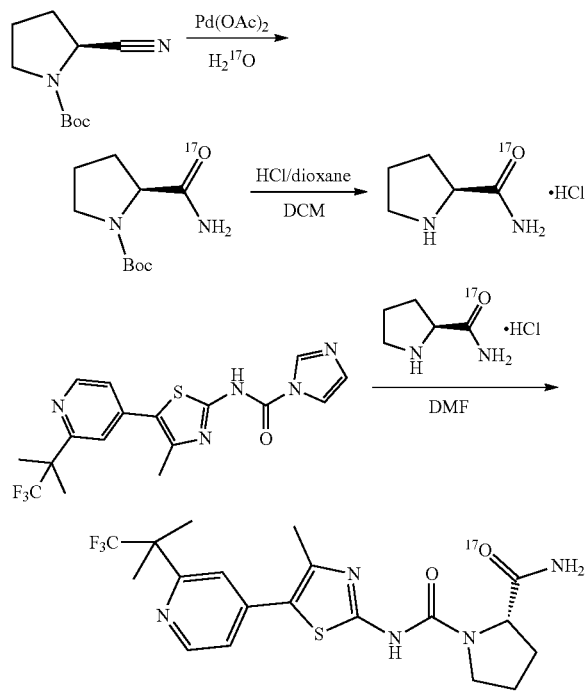

This compound was prepared in the same way as described for Compound 1, starting from O$^{17}$-water (H$_2$$^{17}$O).

Example 3: Preparation of N-(4-methyl-5-(2-(2,2,2-trifluoro-1,1-dimethylethyl)-4 pyridinyl)-2-thiazolyl) aminocarbonyl-L-prolin-$^{13}$C$_1$-amide (Compound 4, or Alpelisib-$^{13}$C$_1$)

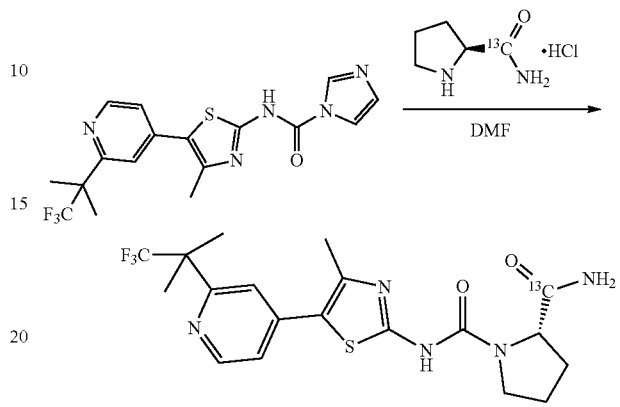

This compound was prepared in the same way as described above, starting from prolin-$^{13}$C$_1$-amide hydrochloride, giving Compound 4.

Example 4: Preparation of N-(4-methyl-5-(2-(2,2,2-trifluoro-1,1-dimethylethyl)-4 pyridinyl)-2-thiazolyl) aminocarbonyl-L-prolinamide-$^{15}$N (Compound 5, or Alpelisib-$^{15}$N)

L-proline (5 g, 43.4 mmol, 1.0 eq), Triethylamine (6.6 g, 65.2 mmol, 1.5 eq.), and (Boc)$_2$O (9.5 g, 43.5 mmol, 1 eq) were added to MeOH (50 mL); the mixture was stirred at 50° C. for 2 hours. Then the solvent was removed under reduced pressure, and the residual material was purified by flash column chromatography (eluent: MeOH/DCM, 1/50), affording N-Boc-L-proline (6.0 g, 64.2%). To a solution of N-Boc-L-proline (1.5 g, 6.97 mmol, 1.0 eq.) in 1,4-dixoane (27 mL) were added pyridine (0.36 mL, 4.20 mmol, 0.6 eq.), $^{15}$N-ammonium sulfate (1.19 g, 8.87 mmol, 1.3 eq), (Boc)$_2$O (1.98 g, 8.87 mmol, 1.3 eq.). The mixture was stirred at 25° C. overnight. The solvent was removed under reduced pressure, and the residual material was purified by flash column chromatography (eluent: DCM/MeOH=100/0-50/1), giving N-Boc-L-prolin-$^{15}$N-amide (0.29 g, enrichment 99.4%). To a solution of N-Boc-L-prolin-$^{15}$N-amide (0.29 g, 1.347 mmol, 1.0 eq) in DCM (3 mL) was added 4 M HCl in dioxane (1.4 mL, 5.6 mmol, 4.16 eq). The mixture was stirred at R. T. for 0.5 h. The precipitate was filtered and dried in vacuum to afford L-prolin-$^{15}$N-amide hydrochloride (0.16 g, enrichment 99.4%). To a solution of 5-(2-(1,1,1-trifluoro-2-methylpropan-2-yl)pyridin-4-yl)thiazol-2-amine (0.5 g, 1.66 mmol) in DCM (25 mL) was added CDI (0.4 g, 2.46 mmol), the mixture was stirred at 40° C. for 4 h. The reaction mixture was cooled to room temperature. The Precipitate was filtered and dried under vacuum to afford N-(4-methyl-5-(2-(1,1,1-trifluoro-2-methylpropan-2-yl)pyridin-4-yl)thiazol-2-yl)-1H-imidazole-1-carboxamide (0.5 g, 76.9%). L-prolin-$^{15}$N-amide hydrochloride (0.16 g, 1.06 mmol, 1.05 eq) was added to a solution of N-(4-methyl-5-(2-(1,1,1-trifluoro-2-methylpropan-2-yl)pyridin-4-yl)thiazol-2-yl)-1H-imidazole-1-carboxamide (400 mg, 1.01 mmol, 1.0 eq) in pyridine (5 ml), followed by addition of DMAP (3 mg, 0.016 mmol, 0.023 eq). The reaction mixture was stirred at 25° C. overnight. Solvent was removed under reduced pressure, and the residual material was purified by flash column chromatography (eluent: DCM/MeOH=100/0-30/1), affording the title compound (240 mg, $^{15}$N-enrichment 99.4%, yield 53.7%): 1H NMR (500 MHz, DMSO-d6) δ ppm 1.64 (s, 6H), 1.90 (s, 3H), 2.12 (s, 1H), 2.44 (s, 3H), 3.50 (s, 1H), 3.63 (s, 1H), 4.31 (s, 1H), 6.99 (m, 1H), 7.42 (m, 2H), 7.58 (s, 1H), 8.63 (s, 1H), 10.96 (s, 1H); 13C NMR (125 MHz, DMSO-d6) δ ppm 16.78, 21.91, 24.39, 30.41, 46.72, 46.92, 60.38, 120.68, 121.71, 125.39, 127.65, 129.90, 132.15, 141.42, 149.53, 159.00, 174.21, 174.32; m/z (ESI$^-$) 440.6, (ESI$^+$) 442.8.

Example 5: Pharmacokinetic Studies of Compound 1 in Sprague Dawley (SD) Rats (a) SD rats, six in a group (n=6), were grouped randomly. Compound 1 (Alpelisib-$^{18}$O$_1$) and Alpelisib were mixed and adjusted to 1:1 molar ratio in dosing solution (1.25 mg/mL); and the dosing solution was administered to the animals, via oral gavage, at a dose level of 2.5 mg/kg. Blood samples were collected at pre-set time points following drug administration, at 0.167, 0.5, 1, 2, 3, 4, 6, 8, and 24 hours (h). The blood samples were converted to plasma samples using standard techniques, and the latter samples were analyzed to determine the concentrations of Compound 1 and Alpelisib. The data are presented in Table 2a and FIG. 1a. In FIG. 1a, lines labelled with -○- and --Δ-- represent the plasma concentrations of Alpelisib-$^{18}$O$_1$ and Alpelisib, respectively, following oral administration of the same molar dose of Alpelisib-$^{18}$O$_1$ and Alpelisib to the animals.

TABLE 2a

PK parameters in SD rats (dose: 2.5 mg/kg).

| Parameter | Unit | Compound 1 | Alpelisib |
|---|---|---|---|
| AUC$_{0-t}$ | ug/L * h | 28719 | 26405 |
| AUC$_{0-\infty}$ | ug/L * h | 28798 | 26476 |
| Tmax | h | 3 | 3 |
| Vz/F | L/kg | 1.655 | 1.798 |
| CLz/F | L/h/kg | 0.434 | 0.472 |
| Cmax | ug/L | 2390 | 2297 |

Figure 1B:
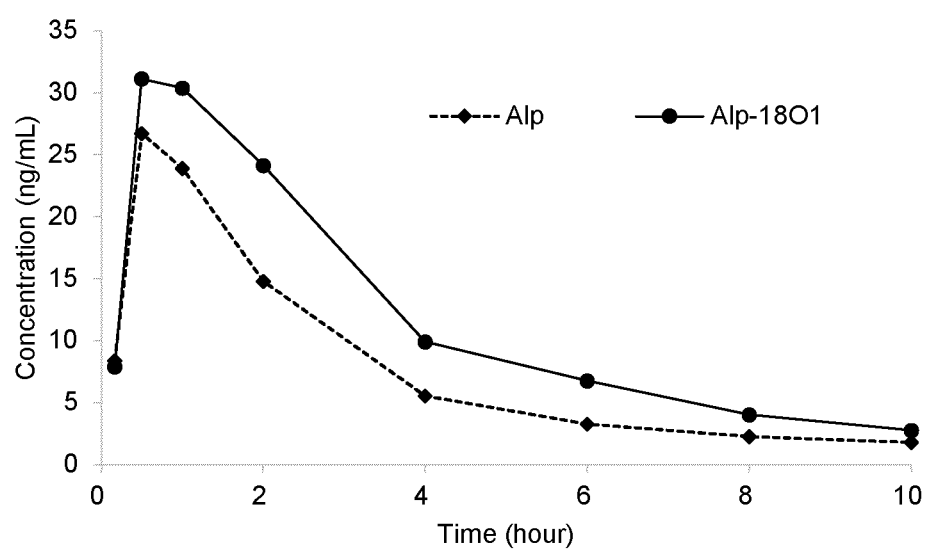

(b) Similarly, Compound 1 (Alpelisib-$^{18}$O$_1$) and Alpelisib were administered to the animals (SD rats, n=4), via oral gavage, at a low dose (dose level of 0.322 mg/kg). Blood samples were collected at pre-set time points following drug administration, at 0.167, 0.5, 1, 2, 4, 6, 8, 10 and 24 hours (h). The blood samples were converted to plasma samples using standard techniques, and the latter samples were analyzed to determine the concentrations of Compound 1 and Alpelisib. At 24-h timepoint, concentrations for both compounds were below the limit of quantification (BLQ); therefore, data from this timepoint were discarded for the purpose of data analysis. The data are presented in Table 2b and FIG. 1b. In FIG. 1b, solid line and dashed line represent the plasma concentrations of Alpelisib-$^{18}$O$_1$ and Alpelisib, respectively.

TABLE 2b

PK parameters in SD rats (dose: 0.322 mg/kg).

| Parameter | Unit | Compound 1 | Alpelisib |
|---|---|---|---|
| AUC$_{0-t}$ | ug/L * h | 117.8 | 75.2 |
| AUC$_{0-\infty}$ | ug/L * h | 131.7 | 80.3 |

TABLE 2b-continued

PK parameters in SD rats (dose: 0.322 mg/kg).

| Parameter | Unit | Compound 1 | Alpelisib |
|---|---|---|---|
| Tmax | h | 0.875 | 0.625 |
| Vz/F | L/kg | 11.4 | 13.1 |
| CLz/F | L/h/kg | 2.5 | 4.1 |
| Cmax | ug/L | 32.6 | 28.1 |

The results show the plasma concentration of Alpelisib-$^{18}$O$_1$ was higher than for Alpelisib after administration under the same conditions. This effect was seen at both doses tested, with the greatest effect seen at low dose.

Example 6: Pharmacokinetic Studies of Compound 1 in ICR Mice

Figure 2:
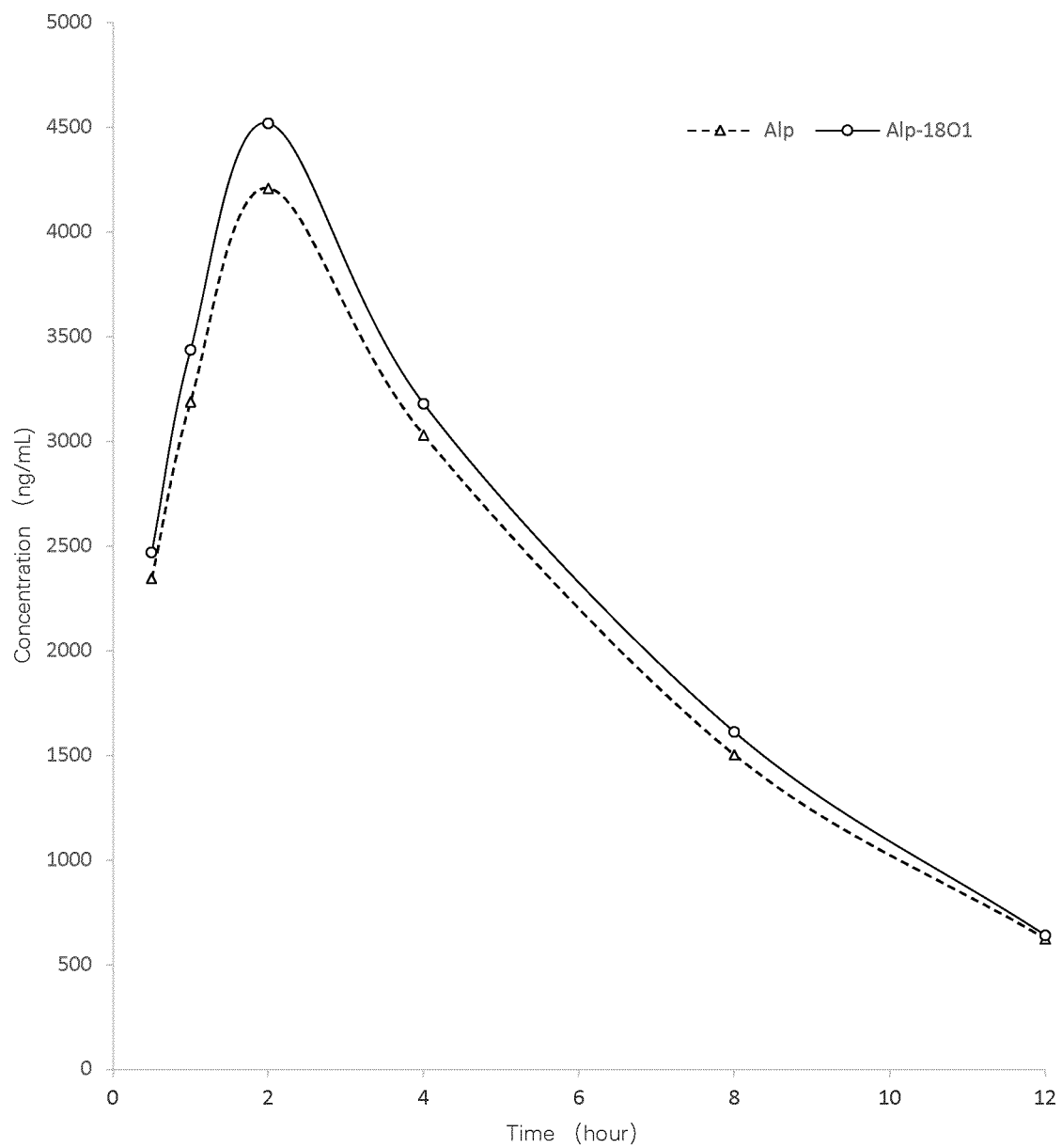
FIG. 2 shows plasma drug concentration-time curves from Alpelisib (-Δ-) and Alpelisib-$^{18}O_1$ (-o-) in ICR mice with oral administration of the same dose of Alpelisib and Alpelisib-$^{18}O_1$.
Figure 3A:
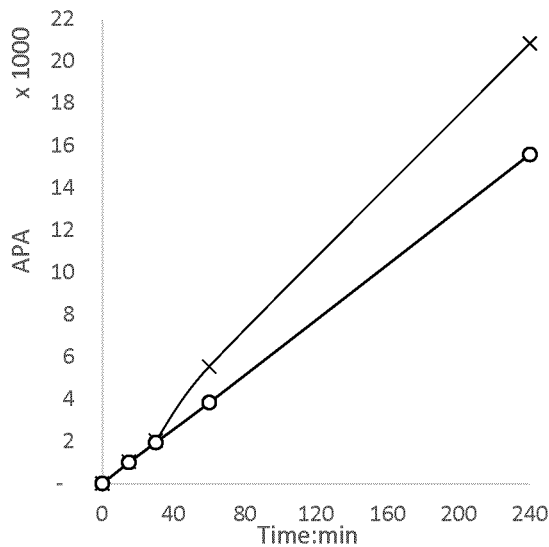
FIGS. 3a, 3b, 3c and 3d show M4 and M4-$^{18}O_1$ production after Alpelisib and Alpelisib-$^{18}O_1$ being incubated in media of liver S9 from various species: (3a) Monkey Liver S9, (3b) Pooled Human S9, (3c) Mini Pig Liver S9, and (3d) Male Wistar Rat Liver S9. In each figure: -x-, M4; -o-, M4-$^{18}O$.
Figure 3B:
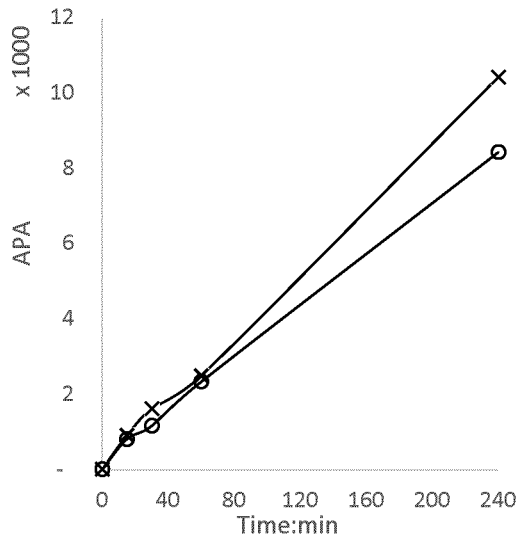
Figure 3C:
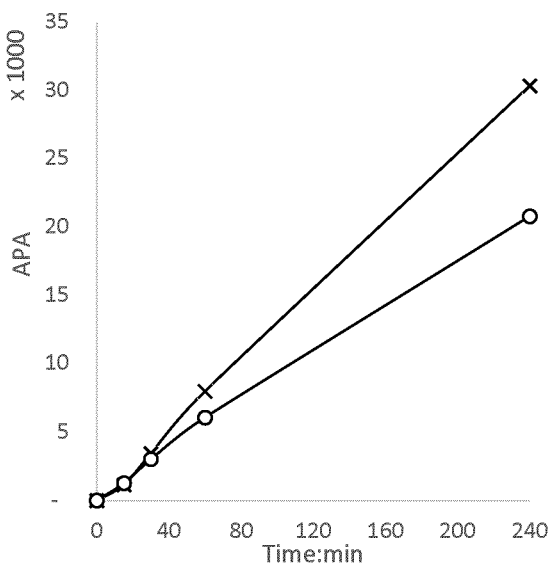
Figure 3D:
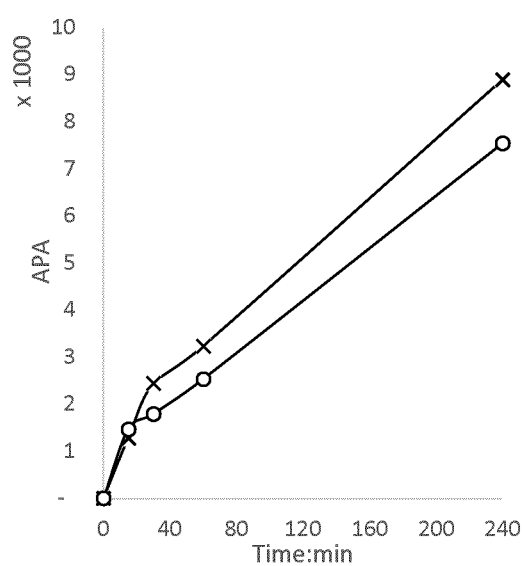

ICR mice, 48, in 6 groups (n=8), were grouped randomly. Compound 1 (Alpelisib-$^{18}$O$_1$) and Alpelisib were mixed and adjusted to 1:1 molar ratio in dosing solution (1.25 mg/mL); and the dosing solution was administered to the animals, via oral gavage, at a dose level of 2.5 mg/kg. Blood samples were collected (a group of 8 animals for each time point) at time points, after dosing, at 0.5, 1, 2, 4, 8, and 12 h. The blood samples were converted to plasma samples using standard techniques, and the latter samples were analyzed to determine the concentrations of Compound 1 and Alpelisib. The data are presented in Table 3 and FIG. 2. In FIG. 2, lines labelled with -○- and --Δ-- represent the plasma concentrations of Alpelisib-$^{18}$O$_1$ and Alpelisib, respectively, following oral administration of the same dose of Alpelisib-$^{18}$O$_1$ and Alpelisib to the animals. The results show the plasma concentration of Alpelisib-$^{18}$O$_1$ was higher than for Alpelisib after administration under the same conditions.

TABLE 3

PK parameters in ICR mice.

| Parameter | Unit | Compound 1 | Alpelisib |
|---|---|---|---|
| AUC(0-t) | ug/L * h | 27845 | 26212 |
| AUC(0-∞) | ug/L * h | 32554 | 30597 |
| Tmax | h | 2 | 2 |
| Vz/F | L/kg | 2.236 | 2.37 |
| CLz/F | L/h/kg | 0.384 | 0.409 |
| Cmax | ug/L | 4519 | 4208 |

Example 7: M4 and M4-$^{18}$O$_1$ Production in Liver S9 Culture Media

The major metabolite of alpelisib is M4, an acid form of the proline derivative, through hydrolysis of the amide bond enzymatically and/or chemically, as shown:

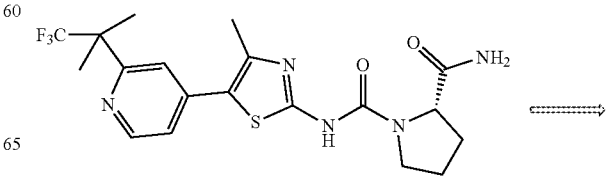

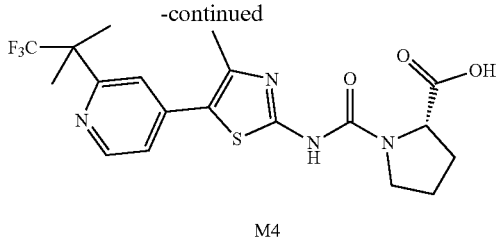

M4

Stock solution (50 μL) containing equal molar concentration of Alpelisib and Alpelisib-$^{18}O_1$ was diluted with pre-warmed (37° C., water bath) 0.1 M Tris-Acetate buffer; and the concentration of each compound in this working solution was 4.5 μM. In each incubation well were added the above working solution (50 μL) and a liver S9 solution (50 μL), mixed well. The sample was pre-incubated for 5 min, following by addition, to each well, of β-NADPH dosing solution (100 μL). The sample plate was incubated at 37° C., and analyzed at time points of 0, 15, 30, 60, and 240 min., in triplicates. Sample analysis: at a pre-set time-point, a stop solution (800 μL, acetonitrile) was added to each well; the sample was well-mixed (Vortex), and centrifuged at 12000 rpm for 5 minutes; the supernatant was transferred to analytical sample vial, and then analyzed with LC-MS/MS, for M4 and M4-$^{18}O_1$. Qualification of the data: in separate experiments under the same analytical conditions, (1) it was confirmed that M4 and M4-$^{18}O_1$ have the same response over the concentration range of the experiment; and (2) no M4 was observed after Alpelisib-$^{18}O_1$ was incubated under the same conditions, indicating no cross-production of M4 and M4-$^{18}O$ from incubation of Compound 1 and Alpelisib. Liver S9 used in the experiment: (a) monkey liver S9, (b) pooled human S9, (c) mini pig liver S9, and (d) male Wistar rat Liver S9. The results of the experiment are summarized in FIGS. 3a-3d.

Figure 4:
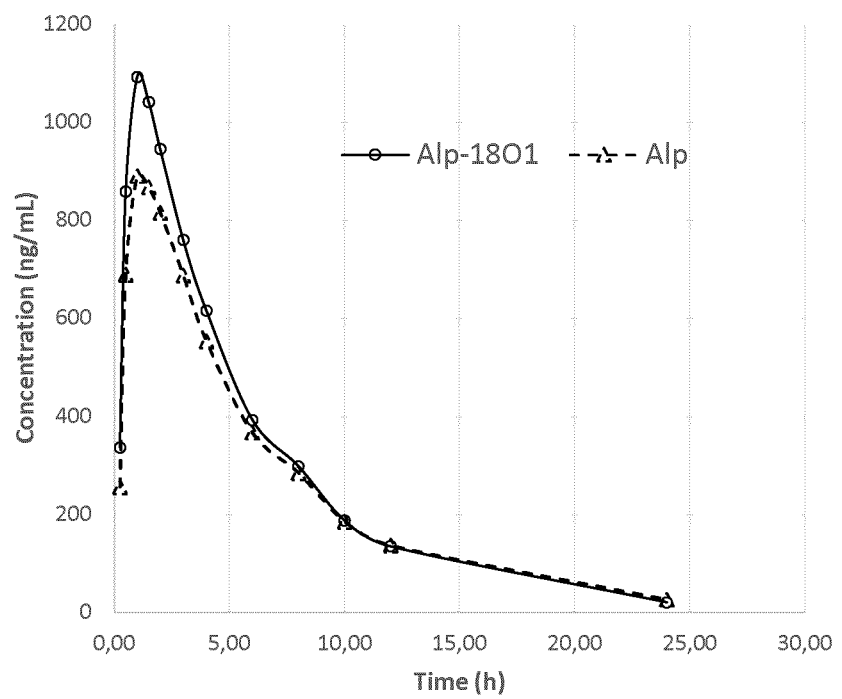
FIG. 4 shows plasma drug concentration-time curves for Alpelisib (-Δ-) and Alpelisib-$^{18}O_1$ (-o-) in beagle dogs with oral administration of the same dose of Alpelisib and Alpelisib-$^{18}O_1$.

The results show that, consistent with the increase in plasma concentration observed for Compound 1 compared to alpelisib, the plasma concentration of the metabolite M4-$^{18}O_1$ from alpelisib-$^{18}O_1$ was decreased compared to that of M4 from the $^{16}O_1$-compound (alpelisib). Moreover, the results confirm that, similar to alpelisib, the main metabolite of Compound 1 was the hydrolysate of the right-end prolinamide group, i.e., N-substituted proline-$^{18}O_1$, or M4-$^{18}O_1$. In addition, only one oxygen atom in the free carboxyl group of the proline derivative was $^{18}O$ (i.e., M4-$^{18}O_1$), indicating that the oxygen-18 atom was not lost during the metabolism of alpelisib-$^{18}O_1$. Taken together, the results indicate that metabolism of Compound 1 was reduced compared to that of Alpelisib Example 8: Pharmacokinetic Studies of Compound 1 in Beagle Dogs Male and female beagle dogs (n=4; 2 males and 2 females) were used in the study. A single oral dose of Alpelisib (2.5 mg/kg) and Compound 1 ($^{18}O_1$-Alpelisib) (2.5 mg/kg) were co-administered (at a total dose of 5 mg/kg) in DMSO and 0.5% carboxymethyl cellulose sodium (CMC-Na) aqueous solution (5:95, v/v). Blood samples were collected for analysis of Alpelisib and $^{18}O_1$-Alpelisib at 0.25, 0.5, 1, 1.5, 2, 3, 4, 6, 8, 10, 12 and 24 h. The data are presented in Table 4 and FIG. 4. In FIG. 4, lines labelled with -o- and -Δ- represent the plasma concentrations of Alpelisib-$^{18}O_1$ and Alpelisib, respectively, following oral administration of the same dose of Alpelisib-$^{18}O_1$ and Alpelisib to the animals. The results show the plasma concentration of Alpelisib-$^{18}O_1$ was higher than for Alpelisib after administration under the same conditions.

TABLE 4

PK parameters in beagle dogs.

| Parameter | Unit | Compound 1 | Alpelisib |
|---|---|---|---|
| $AUC_{(0-t)}$ | ug/L * h | 6682 | 6115 |
| $t_{1/2}$ | h | 4.5 | 5.4 |
| Tmax | h | 1.1 | 1.2 |
| Vz/F | L/kg | 2.4 | 3.0 |
| CLz/F | L/h/kg | 0.38 | 0.41 |
| $C_{max}$ | ug/L | 1468 | 931 |

Taken together, the studies in the above examples show that plasma concentration of Compound 1 was higher than for alpelisib, consistent with reduced metabolism of the prolinamide group and increased bioavailability for Compound 1.

Similar studies were conducted for another isotope-enriched compound, Niraparib-$^{18}O$, in SD rats and in beagle dogs. However, this isotope-enriched compound did not show an increase in plasma concentration and bioavailability compared to Niraparib-$^{16}O$ (data not shown).

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. An isotope-enriched compound of Formula II, or a pharmaceutically acceptable salt, ester, hydrate, chelate, or solvate thereof:

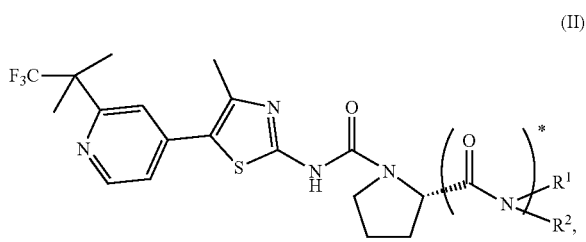

(II)

where:

is an amide functional group isotope-enriched with one or more stable heavy isotope selected from $^{18}O$, $^{17}O$, $^{13}C$, and $^{15}N$; and $R^1$ and $R^2$ are independently a hydrogen or a protecting group selected from acyl, carbonyl, thiocarbonyl, and carbamoyl groups.

2. The isotope-enriched compound of claim 1, wherein the heavy isotope-enriched amide functional group is enriched with $^{18}O$, $^{17}O$, or a mixture of $^{18}O$ and $^{17}O$.

3. The isotope-enriched compound of claim 1, wherein the heavy isotope-enriched amide functional group is enriched with $^{13}C$ or $^{15}N$.

4. The isotope-enriched compound of claim 1, wherein $R^1$ and $R^2$ are hydrogen.

5. The isotope-enriched compound of claim 2, wherein the heavy isotope-enriched amide functional group is enriched with $^{18}O$.

6. The isotope-enriched compound of claim 1, wherein the level of heavy isotope enrichment in the isotope-enriched compound is about 5% or more, about 10% or more, about 20% or more, about 50% or more, about 75% or more, about 90% or more, about 95% or more, or about 98% or more.

7. The isotope-enriched compound of claim 1, wherein the level of isotope-enrichment in the isotope-enriched compound is about 90% or higher, about 91% or higher, about 92% or higher, about 93% or higher, about 94% or higher, about 95% or higher, about 96% or higher, about 97% or higher, about 98% or higher, or about 99% or higher, optionally as determined using mass spectrometry.

8. The isotope-enriched compound of claim 1, wherein the level of isotope-enrichment in the isotope-enriched compound is about 94% or higher or about 95% or higher.

9. A pharmaceutical composition comprising the isotope-enriched compound of claim 1 and a pharmaceutically acceptable carrier.

10. The pharmaceutical composition of claim 9, wherein the composition is in a form suitable for oral administration.

11. The pharmaceutical composition of claim 9, wherein the composition is in the form of a hard shell gelatin capsule, a soft shell gelatin capsule, a cachet, a pill, a tablet, a lozenge, a powder, a granule, a pellet, a pastille, a dragee, a solution, an aqueous liquid suspension, a non-aqueous liquid suspension, an oil-in-water liquid emulsion, a water-in-oil liquid emulsion, an elixir, or a syrup.

12. The pharmaceutical composition of claim 9, wherein the composition is enteric coated or is formulated for controlled release.

13. A method of treatment of a PI3K mediated disease, comprising the step of administering to a subject in need thereof a therapeutically effective amount of the isotope-enriched compound of claim 1, in free form or in pharmaceutically acceptable salt form.

14. A method of treatment of a PI3K mediated disease, comprising the step of administering to a subject in need thereof a therapeutically effective amount of the pharmaceutical composition of claim 9.

15. The method of claim 13, wherein the PI3K mediated disease is a proliferative disease.

16. The method of claim 15, wherein the proliferative disease is melanoma, colorectal adenoma, breast cancer, or pancreatic cancer.

17. The method of claim 16, wherein the breast cancer is hormone receptor positive (HR$^+$) and human epidermal growth factor receptor negative (HER2$^-$).

18. The method of claim 17, wherein the breast cancer is PIK3CA mutated.

19. The method of claim 13, wherein the method further comprises administration of a therapeutically effective amount of fulvestrant.

20. The method of claim 13, wherein the isotope-enriched compound is administered orally, optionally in the form of a tablet.

* * * * *